US012703709B2

(12) United States Patent
Huang et al.

(10) Patent No.: US 12,703,709 B2
(45) Date of Patent: Aug. 11, 2026

(54) CEPHALOSPORIN ANTIBACTERIAL COMPOUND AND PREPARATION METHOD THEREFOR

(71) Applicants: SHANGHAI SENHUI MEDICINE CO., LTD., Shanghai (CN); SHANGHAI SHENGDI PHARMACEUTICAL CO., LTD., Shanghai (CN); JIANGSU HENGRUI PHARMACEUTICALS CO., LTD., Lianyungang (CN)

(72) Inventors: Jian Huang, Shanghai (CN); Lingjian Zhu, Shanghai (CN); Yang Zou, Shanghai (CN); Cili Zhang, Shanghai (CN)

(73) Assignees: Shanghai Senhui Medicine Co., Ltd., Shanghai (CN); Shanghai Shengdi Pharmaceutical Co., Ltd., Shanghai (CN); Jiangsu Hengrui Pharmaceuticals Co., Ltd., Lianyungang (CN)

( * ) Notice: Subject to any disclaimer, the term of this patent is extended or adjusted under 35 U.S.C. 154(b) by 419 days.

(21) Appl. No.: 18/272,071

(22) PCT Filed: Jan. 12, 2022

(86) PCT No.: PCT/CN2022/071527

§ 371 (c)(1),
(2) Date: Jul. 12, 2023

(87) PCT Pub. No.: WO2022/152146

PCT Pub. Date: Jul. 21, 2022

(65) Prior Publication Data

US 2024/0132518 A1 Apr. 25, 2024

(30) Foreign Application Priority Data

Jan. 12, 2021 (CN) ......................... 202110038012.3
Jun. 11, 2021 (CN) ......................... 202110655016.6

(51) Int. Cl.
*C07D 501/28* (2006.01)
*A61P 31/04* (2006.01)

(52) U.S. Cl.
CPC ............ *C07D 501/28* (2013.01); *A61P 31/04* (2018.01)

(58) Field of Classification Search
CPC .............................. C07D 501/28; A61P 31/04
See application file for complete search history.

(56) References Cited

FOREIGN PATENT DOCUMENTS

| | | | |
|---|---|---|---|
| CN | 102918047 | A | 2/2013 |
| CN | 102918048 | A | 2/2013 |
| CN | 102203100 | A | 8/2014 |
| CN | 104884460 | A | 9/2015 |
| JP | 2015221788 | A | 12/2015 |
| WO | 2021147986 | A1 | 7/2021 |

*Primary Examiner* — Alicia L Otton
(74) *Attorney, Agent, or Firm* — Morgan, Lewis & Bockius LLP

(57) ABSTRACT

The present disclosure relates to a cephalosporin antibacterial compound and a preparation method therefor. The cephalosporin antibacterial compound can exhibit antibacterial activity against Gram-negative bacteria and other bacteria.

18 Claims, No Drawings

CEPHALOSPORIN ANTIBACTERIAL COMPOUND AND PREPARATION METHOD THEREFOR

CROSS-REFERENCE TO RELATED APPLICATIONS

The present application is a national stage application of International Patent Application No. PCT/CN2022/071527, filed Jan. 12, 2022, which claims the benefit of and priority to Chinese Patent Application No. 202110655016.6, filed on Jun. 11, 2021 and Chinese Patent Application No. 202110038012.3, filed on Jan. 12, 2021, all of which are incorporated herein by reference in their entirety.

TECHNICAL FIELD

The present disclosure belongs to the field of pharmaceutics, and particularly relates to a cephalosporin antibacterial compound and a preparation method therefor.

BACKGROUND

The development of antibacterial treatment regimens has been an ongoing challenge for today's society. The antibacterial agents include various chemically synthesized drugs such as antibiotics, sulfonamides, imidazoles, nitroimidazoles and quinolones, among which β-lactam antibiotics are a very important class. As yet, a number of β-lactamase drugs have been reported in the literature or have been available on the market. They have become very important clinical antibacterial drugs. However, resistance to β-lactam drugs is a growing problem, and an increasing number of bacteria have acquired resistance by producing β-lactamases and degrading β-lactamase drugs.

β-lactamases are mainly classified into 4 types according to the Ambler molecular classification, specifically including A type (TEM type, SHV type, CTX-M type, KPC type, etc.), B type (IMP type, VIM type, L-1 type, etc.), C type (AmpC type), and D type (OXA type, etc.). Among those types, A, C and D types mainly belong to serine-β-lactamases, and B type belongs to metallo-β-lactamases, both having their own different mechanisms in hydrolyzing β-lactamase drugs.

The emergence of gram-negative bacteria that become highly resistant to β-lactamase drugs (including cephalosporins and carbapenems) by producing A-type or D-type serine β-lactamases and B-type metallo-β-lactamases that extend their substrate spectrum poses a significant clinical problem. It is known that metallo-β-lactamase is one of the causes for gram-negative bacteria to acquire multi-drug resistance, however, the development of cephalosporin compounds with more effective antibacterial activity, especially ones showing efficacy on gram-negative bacteria producing various β-lactamases, is a challenge in the research field of antibacterial agents today.

It has been reported in the literature (Antimicrob Agents Chemother. 1982, 22(2), 181-185.) that cephalosporin compounds containing a catechol group in the molecule have high activity against gram-negative bacteria. The mechanism of action is that the catechol group in the molecule forms a chelate with extracellular $Fe^{3+}$, so that the compound is effectively incorporated into the bacteria through a $Fe^{3+}$ transport system (tonB-dependent transport system) on the cell membrane. This Trojan horse strategy allows the compound to have a higher concentration in the periplasmic space (the narrow space between the outer membrane and the cell wall), and to bind a receptor to inhibit the synthesis of the bacterial cell wall. Therefore, compounds having catechol or a similar structure in the 3-position side chain or 7-position side chain of a cephalosporin skeleton have been studied (EP0416410B1). Cefiderocol is a novel siderophore cephalosporin (WO2010050468, WO2017216765, Eur. J Med. Chem. 2018, 155, 847-868.), and up to now, Fetroja (cefiderocol) from Shionogi Pharmaceutical has been approved by the FDA (U.S. Food and Drug Administration) for treating complicated urinary tract infection (cUTI) including kidney infections caused by sensitive gram-negative bacteria, in patients aged 18 or older.

SUMMARY

The present disclosure is intended to provide a cephalosporin antibacterial compound capable of exhibiting an effective antibacterial spectrum against a variety of bacteria such as gram-negative bacteria.

One aspect of the present disclosure provides a compound of formula I or a pharmaceutically acceptable salt thereof,

I

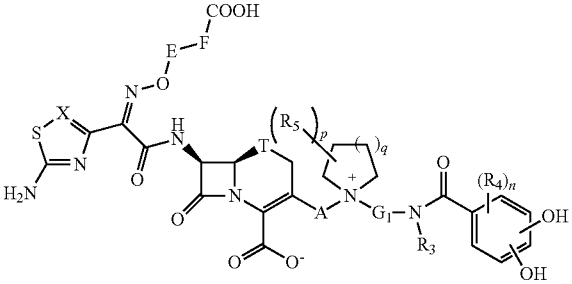

wherein,

X is N, CH or C—Cl;

T is S, S═O, $CH_2$ or O;

E is

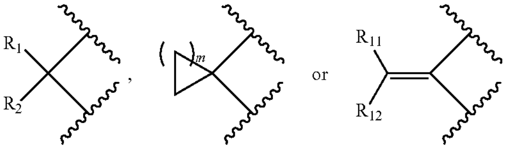

wherein $R_1$ and $R_2$ are each independently selected from the group consisting of hydrogen, halogen, phenyl, alkylthio, and alkyl optionally substituted with carbamoyl; $R_{11}$ and $R_{12}$ are each independently selected from the group consisting of hydrogen, carboxyl, and alkyl optionally substituted with carbamoyl; m is an integer of 1-5;

F is a single bond;

A is $C_1$-$C_6$ alkylene, $C_2$-$C_6$ alkenylene or $C_2$-$C_6$ alkynylene;

each $R_5$ is independently selected from the group consisting of halogen, hydroxy, $C_1$-$C_6$ alkyl, $C_1$-$C_6$ alkoxy, $C_1$-$C_6$ haloalkyl and $C_1$-$C_6$ haloalkoxy;

$G_1$ is

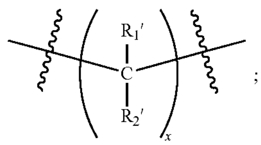

$R_1$' and $R_2$' are each independently selected from the group consisting of hydrogen, halogen, hydroxy, $C_1$-$C_6$ alkyl, $C_1$-$C_6$ alkoxy, $C_1$-$C_6$ haloalkyl and $C_1$-$C_6$ haloalkoxy;

$R_3$ is $C_1$-$C_6$ alkyl substituted with

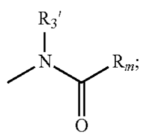

$R_3$' is selected from the group consisting of hydrogen, hydroxy, $C_1$-$C_6$ alkyl and $C_1$-$C_6$ alkoxy, wherein the alkyl and alkoxy are optionally substituted with one or more substituents selected from the group consisting of $C_1$-$C_6$ alkyl, halogen, hydroxy, sulfhydryl, —$NR_iR_j$,

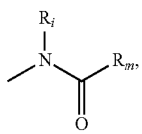

oxo, thio, —C(O)$R_k$, —C(O)O$R_k$, —C(S)$R_k$, nitro, cyano, $C_1$-$C_6$ alkoxy and $C_1$-$C_6$ alkylthioether group;

each $R_m$ is independently selected from the group consisting of hydrogen, $C_1$-$C_6$ alkyl, $C_1$-$C_6$ alkoxy, hydroxy, 6- to 10-membered aryl and 5- to 8-membered heteroaryl, wherein the alkyl, alkoxy, aryl and heteroaryl are optionally substituted with one or more substituents selected from the group consisting of $C_1$-$C_6$ alkyl, halogen, hydroxy, sulfhydryl, amino, carboxyl, nitro, cyano and $C_1$-$C_6$ alkoxy;

each $R_4$ is independently selected from the group consisting of halogen, hydroxy, sulfhydryl and —$NR_iR_j$;

$R_i$ and $R_j$ are each independently selected from the group consisting of hydrogen, hydroxy, $C_1$-$C_6$ alkyl and $C_1$-$C_6$ alkoxy;

each $R_k$ is independently selected from the group consisting of hydrogen, $C_1$-$C_6$ alkyl, $C_1$-$C_6$ haloalkyl, hydroxy, $C_1$-$C_6$ alkoxy and —$NR_iR_j$, wherein the alkyl, haloalkyl and alkoxy are optionally substituted with one or more substituents selected from the group consisting of $C_1$-$C_6$ alkyl, halogen, hydroxy, sulfhydryl, —$NR_iR_j$, oxo, thio, carboxyl, nitro, cyano, $C_1$-$C_6$ alkoxy, $C_1$-$C_6$ alkylthioether group, 3- to 6-membered cycloalkyl, 3- to 6-membered heterocyclyl, 6- to 10-membered aryl and 5- to 8-membered heteroaryl;

p is an integer of 0-5;

q is an integer of 0-5;

x is an integer of 3-8;

n is an integer of 0-3.

The "C" in the formula is a carbon atom.

In certain embodiments, E is

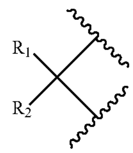

wherein $R_1$ and $R_2$ are each independently selected from the group consisting of hydrogen, halogen, and alkyl optionally substituted with carbamoyl.

In certain embodiments, A is $C_1$-$C_6$ alkylene.

In certain embodiments, $R_1$' and $R_2$' are both hydrogen atoms.

In certain embodiments, x is an integer of 3-6.

In certain embodiments, $R_3$ is selected from $C_3$-$C_6$ alkyl substituted with

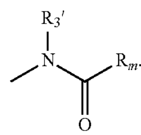

In certain embodiments,

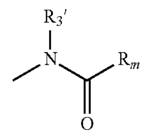

is

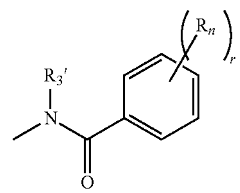

wherein each $R_n$ is independently selected from the group consisting of $C_1$-$C_6$ alkyl, hydroxy and halogen, and r is independently an integer of 0-5; preferably

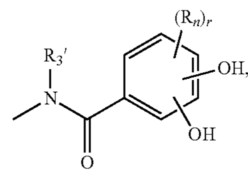

wherein r is independently an integer of 0-3; and more preferably

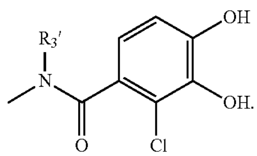

In certain embodiments, $R_3'$ is selected from the group consisting of hydrogen and $C_1$-$C_6$ alkyl substituted with

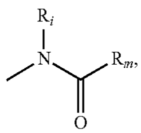

preferably hydrogen and $C_3$-$C_6$ alkyl substituted with

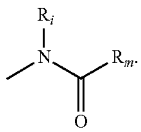

In certain embodiments,

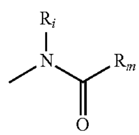

is

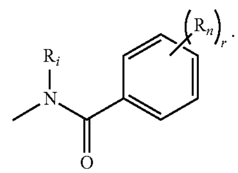

wherein each $R_n$ is independently selected from the group consisting of $C_1$-$C_6$ alkyl, hydroxy and halogen, and r is independently an integer of 0-5; preferably

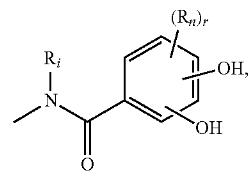

wherein r is independently an integer of 0-3; and more preferably

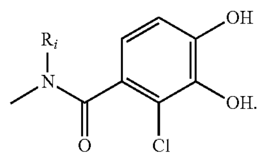

In certain embodiments, the compound of formula I is selected from

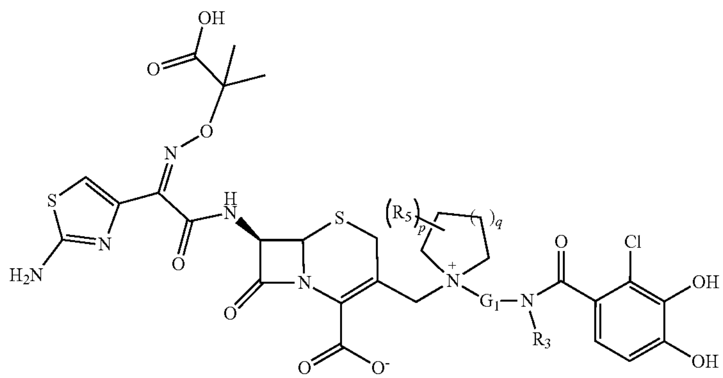

or a pharmaceutically acceptable salt thereof.

In certain embodiments, the compound is selected from

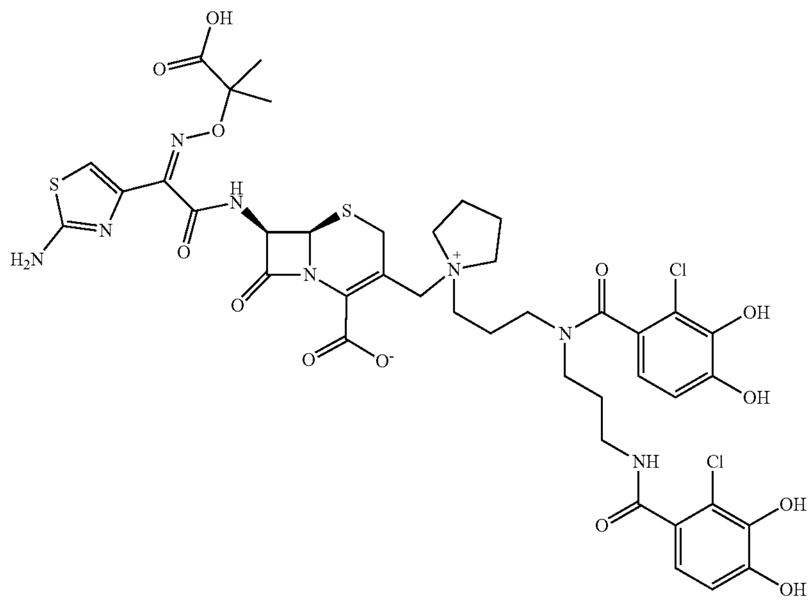

or a pharmaceutically acceptable salt thereof.

The "alkyl" described herein is preferably $C_1$-$C_6$ alkyl.

The "alkylene" described herein is preferably $C_1$-$C_6$ alkylene.

The "alkenylene" described herein is preferably $C_2$-$C_6$ alkenylene.

The "alkynylene" described herein is preferably $C_2$-$C_6$ alkynylene.

The "alkoxy" described herein is preferably $C_1$-$C_6$ alkoxy.

The "alkylthioether group" described herein is preferably $C_1$-$C_6$ alkylthioether group.

The "cycloalkyl" described herein is preferably 3- to 12-membered cycloalkyl, and more preferably 3- to 6-membered cycloalkyl.

The "fused cycloalkyl" described herein is preferably 6- to 14-membered fused cycloalkyl, and more preferably 7- to 10-membered fused cycloalkyl.

The "heterocyclyl" described herein is preferably 3- to 12-membered heterocyclyl, and more preferably 3- to 6-membered heterocyclyl.

The "fused heterocyclyl" described herein is preferably 6- to 14-membered fused heterocyclyl, and more preferably 7- to 10-membered fused heterocyclyl.

The "aryl" described herein is preferably 6- to 14-membered aryl, and more preferably 6- to 10-membered aryl.

The "fused cycloaryl" described herein is preferably 8- to 14-membered fused cycloaryl, and more preferably 8- to 12-membered fused cycloaryl.

The "heteroaryl" described herein is preferably 5- to 12-membered heteroaryl, and more preferably 5- to 8-membered heteroaryl.

The "fused heteroaryl" described herein is preferably 5- to 14-membered fused heteroaryl, and more preferably 5- to 12-membered fused heteroaryl.

In certain embodiments, the compound of the present disclosure is in the Z configuration.

The present disclosure also provides a pharmaceutical composition comprising at least one of the compounds or the pharmaceutically acceptable salt thereof described above, and a pharmaceutically acceptable carrier, diluent or excipient.

In certain embodiments, the pharmaceutical composition is in unit dose of 0.001-1000 mg.

In certain embodiments, the pharmaceutical composition comprises 0.01%-99.99% of the compound described above based on the total weight of the composition. In certain embodiments, the pharmaceutical composition comprises 0.1%-99.9% of the compound described above. In certain embodiments, the pharmaceutical composition comprises 0.5%-99.5% of the compound described above. In certain embodiments, the pharmaceutical composition comprises 1%-99% of the compound described above. In certain embodiments, the pharmaceutical composition comprises 2%-98% of the compound described above.

In certain embodiments, the pharmaceutical composition comprises 0.01%-99.99% of a pharmaceutically acceptable carrier, diluent or excipient based on the total weight of the composition. In certain embodiments, the pharmaceutical composition comprises 0.1%-99.9% of a pharmaceutically acceptable carrier, diluent or excipient. In certain embodiments, the pharmaceutical composition comprises 0.5%-99.5% of a pharmaceutically acceptable carrier, diluent or excipient. In certain embodiments, the pharmaceutical composition comprises 1%-99% of a pharmaceutically acceptable carrier, diluent or excipient. In certain embodiments, the pharmaceutical composition comprises 2%-98% of a pharmaceutically acceptable carrier, diluent or excipient.

The present disclosure also provides use of the compound or the pharmaceutically acceptable salt thereof of the present disclosure for preventing and treating a disease caused by pathogenic bacteria in a mammal, including a human. The use is, for example, to treat airway infectious diseases, urinary system infectious diseases, respiratory system infectious diseases, septicemia, nephritis, cholecystitis, oral infectious diseases, endocarditis, pneumonia, bone marrow membrane myelitis, otitis media, enteritis, empyema, traumatic infectious diseases, opportunistic infections, and the like.

The present disclosure also provides use of the compound or the pharmaceutically acceptable salt thereof of the present disclosure for preventing and treating a disease caused by gram-negative bacteria. The gram-negative bacteria are preferably gram-negative bacteria of intestinal bacteria (*E. coli, Klebsiella, Serratia, Enterobacter, Citrobacter, Morganella, Providencia, Proteus*, etc.), gram-negative bacteria residing in the respiratory system (*Haemophilus, Moraxella*, etc.), and glucose nonfermenting gram-negative bacteria (*Pseudomonas aeruginosa, Pseudomonas* other than *P. aeruginosa, Stenotrophomonas, Burkholderia, Acinetobacter*, etc.).

The present disclosure also provides use of the compound or the pharmaceutically acceptable salt thereof of the present disclosure for preventing and treating a disease caused by gram-positive bacteria.

The present disclosure further provides a method for treating the diseases described above in a mammal, and the mammal may be a human or a non-human mammal; the method, for therapeutic purposes, comprises administering to the mammal the compound or the pharmaceutically acceptable salt thereof, or the pharmaceutical composition of the present disclosure.

The present disclosure further provides a kit comprising the compound or the pharmaceutically acceptable salt thereof, or the pharmaceutical composition of the present disclosure.

According to the test method well known in the art (e.g., WO2010050468), the compound of the present disclosure is determined to have inhibitory activity against gram-negative bacteria and have excellent efficacy.

Terms and Definitions

Unless otherwise stated, the terms used in the specification and claims have the following meanings.

The term "alkyl" refers to a saturated aliphatic hydrocarbon group which is a linear or branched group containing 1 to 20 carbon atoms, preferably an alkyl group containing 1 to 12 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof, and the like. More preferred is an alkyl group containing 1 to 6 carbon atoms; non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl may be substituted or unsubstituted, and when it is substituted, the substituent may be substituted at any available point of attachment, and the substituent is preferably one or more groups independently selected from the group consisting of alkyl, alkenyl, alkynyl, alkoxy, alkylthio, alkylamino, halogen, sulfhydryl, hydroxy, nitro, cyano, cycloalkyl, heterocycloalkyl, aryl, heteroaryl, cycloalkoxy, heterocycloalkoxy, cycloalkylthio, heterocycloalkylthio, oxo, carboxyl and a carboxylate group.

The term "alkylene" refers to a saturated linear or branched aliphatic hydrocarbon group having 2 residues derived from the parent alkane by removal of two hydrogen atoms from the same carbon atom or two different carbon atoms. It is a linear or branched group containing 1 to 20 carbon atoms, preferably alkylene containing 1 to 12 carbon atoms, and more preferably alkylene containing 1 to 6 carbon atoms. Non-limiting examples of alkylene include, but are not limited to, methylene ($—CH_2—$), 1,1-ethylene ($—CH(CH_3)—$), 1,2-ethylene ($—CH_2CH_2—$), 1,1-propylene ($—CH(CH_2CH_3)—$), 1,2-propylene ($—CH_2CH(CH_3)—$), 1,3-propylene ($—CH_2CH_2CH_2—$), 1,4-butylene ($—CH_2CH_2CH_2CH_2—$), and the like. The alkylene may be substituted or unsubstituted, and when it is substituted, the substituent may be substituted at any available point of attachment.

The term "alkenylene" refers to a linear alkenyl group having 2 to 8 carbon atoms, preferably 2 to 6 carbon atoms, and more preferably 2 to 4 carbon atoms, and having at least one double bond at any positions, including, for example, ethenylene, allylene, propenylene, butenylene, prenylene, butadienylene, pentenylene, pentadienylene, hexenylene, hexadienylene, and the like.

The term "alkynylene" refers to a linear alkynylene group having 2 to 8 carbon atoms, preferably 2 to 6 carbon atoms, and more preferably 2 to 4 carbon atoms, and having at least one triple bond at any positions, including, for example, ethynylene, propynylene, butynelene, pentynylene, hexynylene, and the like.

The term "cycloalkyl" refers to a saturated or partially unsaturated monocyclic or polycyclic hydrocarbon substituent. The cycloalkyl ring contains 3 to 20 carbon atoms, preferably 3 to 12 carbon atoms, and more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. Polycyclic cycloalkyl includes spiro cycloalkyl, fused cycloalkyl, and bridged cycloalkyl.

The term "spiro cycloalkyl" refers to a 5- to 20-membered polycyclic group in which monocyclic rings share one carbon atom (referred to as the spiro atom). It may contain one or more double bonds, but none of the rings has a fully conjugated π-electron system. It is preferably 6- to 14-membered, and more preferably 7- to 10-membered. According to the number of the spiro atoms shared among the rings, the spiro cycloalkyl may be monospiro cycloalkyl, bispiro cycloalkyl or polyspiro cycloalkyl, preferably monospiro cycloalkyl and bispiro cycloalkyl, and more preferably 4-membered/4-membered, 4-membered/5-membered, 4-membered/6-membered, 5-membered/5-membered or 5-membered/6-membered monospiro cycloalkyl. Non-limiting examples of spiro cycloalkyl include:

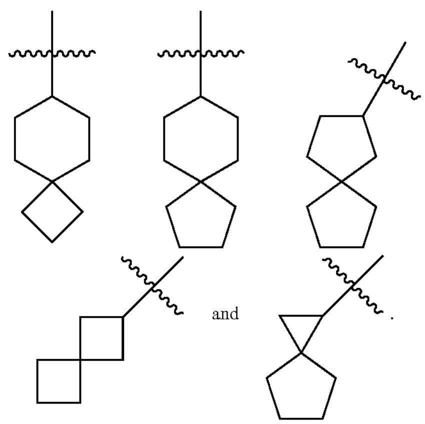

The term "fused cycloalkyl" refers to a 5- to 20-membered all-carbon polycyclic group in which each ring in the system shares a pair of adjacent carbon atoms with other rings in the system, wherein one or more rings may contain one or more double bonds, but none of them has a fully conjugated π-electron system. It is preferably 6- to 14-membered, and more preferably 7- to 10-membered. According to the number of constituent rings, the fused cycloalkyl may be bicyclic, tricyclic, tetracyclic or polycyclic fused cycloalkyl, preferably bicyclic or tricyclic fused cycloalkyl, and more preferably 5-membered/5-membered or 5-membered/6-membered bicycloalkyl. Non-limiting examples of fused cycloalkyl include:

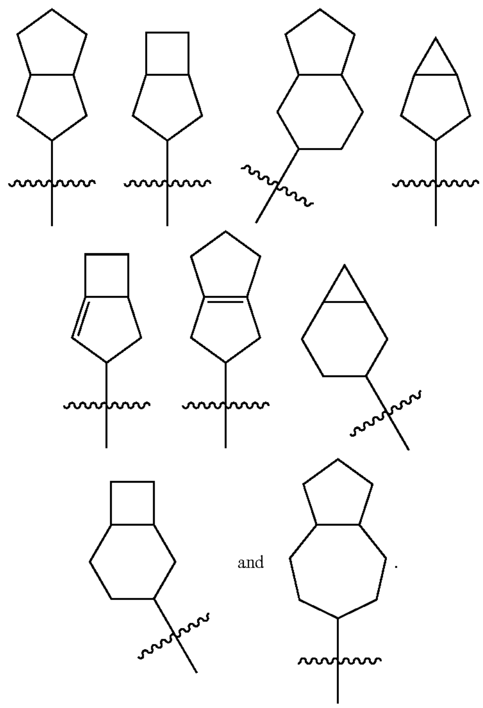

The term "bridged cycloalkyl" refers to a 5- to 20-membered all-carbon polycyclic group in which any two rings share two carbon atoms that are not directly connected to each other. It may contain one or more double bonds, but none of the rings has a fully conjugated π-electron system. It is preferably 6- to 14-membered, and more preferably 7- to 10-membered. According to the number of constituent rings, the bridged cycloalkyl may be bicyclic, tricyclic, tetracyclic or polycyclic bridged cycloalkyl, preferably bicyclic, tricyclic or tetracyclic bridged cycloalkyl, and more preferably bicyclic or tricyclic bridged cycloalkyl. Non-limiting examples of bridged cycloalkyl include:

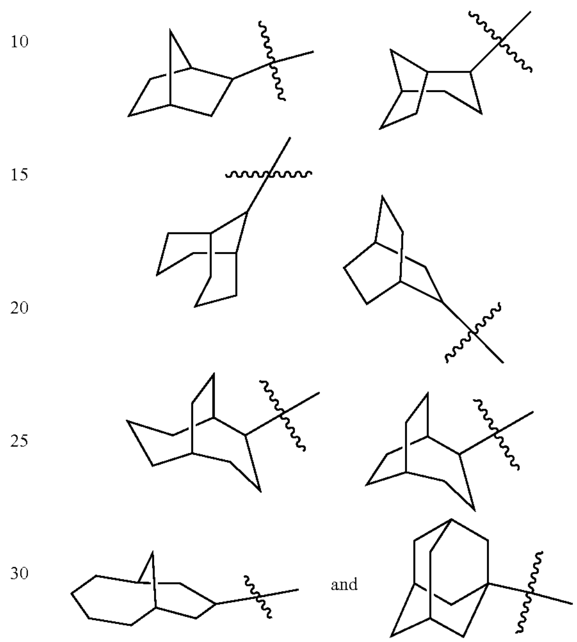

The cycloalkyl ring may be fused to an aryl, heteroaryl or heterocycloalkyl ring, wherein the ring attached to the parent structure is cycloalkyl; non-limiting examples include indanyl, tetrahydronaphthyl, benzocycloheptyl, and the like. The cycloalkyl may be optionally substituted or unsubstituted, and when it is substituted, the substituent is preferably one or more groups independently selected from the group consisting of alkyl, alkenyl, alkynyl, alkoxy, alkylthio, alkylamino, halogen, sulfhydryl, hydroxy, nitro, cyano, cycloalkyl, heterocycloalkyl, aryl, heteroaryl, cycloalkoxy, heterocycloalkoxy, cycloalkylthio, heterocycloalkylthio, oxo, carboxyl and a carboxylate group.

The term "heterocyclyl" refers to a saturated or partially unsaturated monocyclic or polycyclic hydrocarbon substituent containing 3 to 20 ring atoms, one or more of which are heteroatoms selected from the group consisting of nitrogen, oxygen and $S(O)_m$ (where m is an integer of 0 to 2), excluding a ring moiety of —O—O—, —O—S— or —S—S—, and the remaining ring atoms are carbon atoms. It preferably contains 3 to 12 ring atoms, of which 1 to 4 are heteroatoms; more preferably, it contains 3 to 6 ring atoms. Non-limiting examples of monocyclic heterocyclyl include pyrrolidinyl, imidazolidinyl, tetrahydrofuranyl, tetrahydrothienyl, dihydroimidazolyl, dihydrofuranyl, dihydropyrazolyl, dihydropyrrolyl, piperidinyl, piperazinyl, morpholinyl, thiomorpholinyl, homopiperazinyl, and the like, preferably piperidinyl and pyrrolidinyl. Polycyclic heterocyclyl includes spiro heterocyclyl, fused heterocyclyl, and bridged heterocyclyl.

The term "spiro heterocyclyl" refers to a 5- to 20-membered polycyclic heterocyclyl group in which monocyclic rings share one atom (referred to as the spiro atom), wherein one or more ring atoms are heteroatoms selected from the group consisting of nitrogen, oxygen and $S(O)_m$ (where m is an integer of 0 to 2), and the remaining ring atoms are carbon atoms. It may contain one or more double bonds, but none of the rings has a fully conjugated π-electron system. It is preferably 6- to 14-membered, and more preferably 7- to 10-membered. According to the number of spiro atoms shared among the rings, the spiro heterocyclyl may be monospiro heterocyclyl, bispiro heterocyclyl or polyspiro heterocyclyl, preferably monospiro heterocyclyl and bispiro heterocyclyl, and more preferably 4-membered/4-membered, 4-membered/5-membered, 4-membered/6-membered, 5-membered/5-membered or 5-membered/6-membered monospiro heterocyclyl. Non-limiting examples of spiro heterocyclyl include:

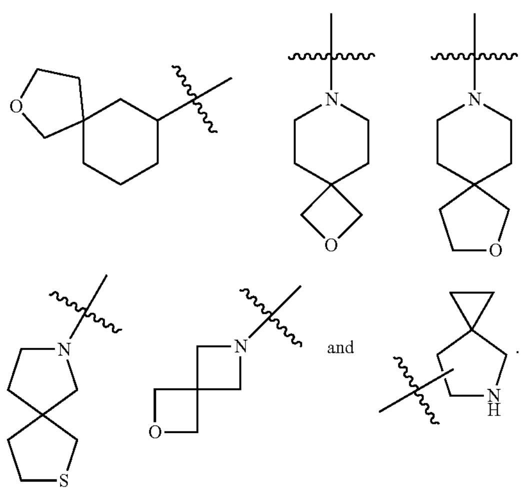

and

The term "fused heterocyclyl" refers to a 5- to 20-membered polycyclic heterocyclyl group in which each ring shares a pair of adjacent atoms with the other rings in the system, wherein one or more of the rings may contain one or more double bonds, but none of them has a fully conjugated π-electron system, and one or more of the ring atoms are heteroatoms selected from the group consisting of nitrogen, oxygen or $S(O)_m$ (where m is an integer of 0 to 2), and the remaining ring atoms are carbon atoms. It is preferably 6- to 14-membered, and more preferably 7- to 10-membered. According to the number of constituent rings, the fused heterocyclyl may be bicyclic, tricyclic, tetracyclic or polycyclic fused heterocyclyl, preferably bicyclic or tricyclic fused heterocyclyl, and more preferably 5-membered/5-membered or 5-membered/6-membered bicyclic fused heterocyclyl. Non-limiting examples of fused heterocyclyl include:

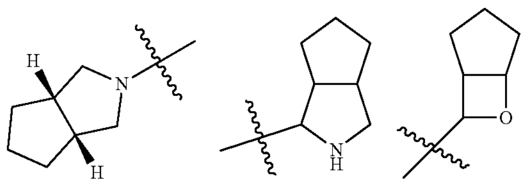

-continued

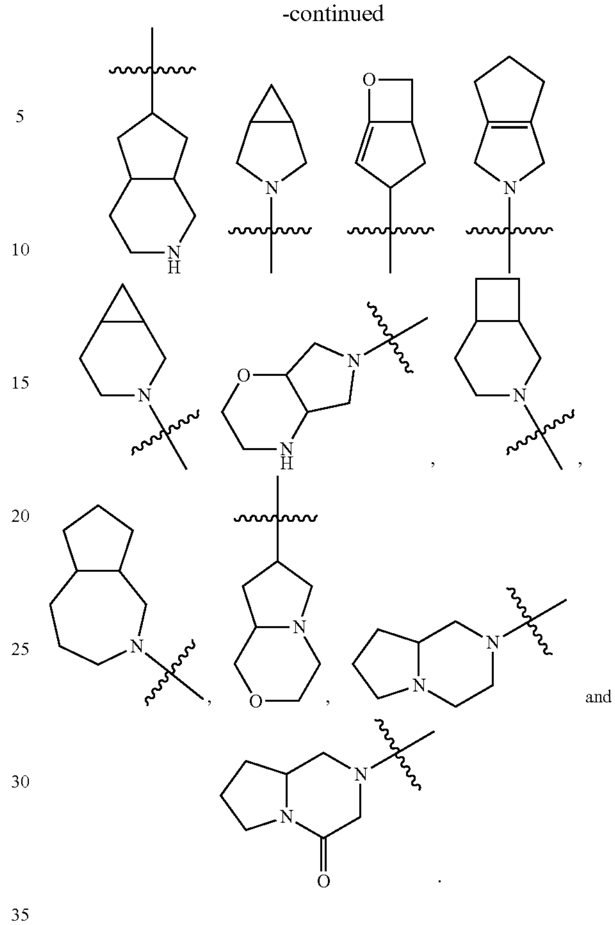

and

The term "bridged heterocyclyl" refers to a 5- to 14-membered polycyclic heterocyclyl group in which any two rings share two atoms that are not directly connected to each other. It may contain one or more double bonds, but none of the rings has a fully conjugated π-electron system, wherein one or more of the ring atoms are heteroatoms selected from the group consisting of nitrogen, oxygen and $S(O)_m$ (where m is an integer of 0 to 2), and the remaining ring atoms are carbon atoms. It is preferably 6- to 14-membered, and more preferably 7- to 10-membered. According to the number of constituent rings, the bridged heterocyclyl may be bicyclic, tricyclic, tetracyclic or polycyclic bridged heterocyclyl, preferably bicyclic, tricyclic or tetracyclic bridged heterocyclyl, and more preferably bicyclic or tricyclic bridged heterocyclyl. Non-limiting examples of bridged heterocyclyl include:

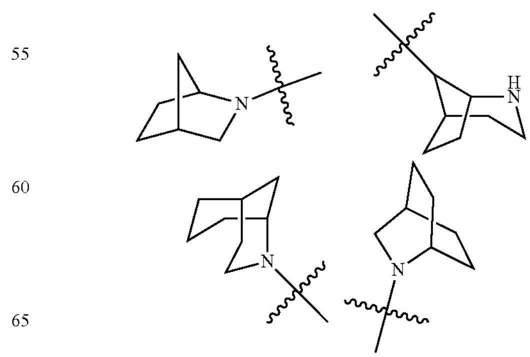

-continued

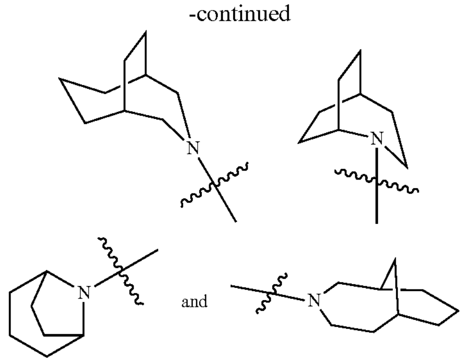

The heterocyclyl ring may be fused to an aryl, heteroaryl or cycloalkyl ring, wherein the ring attached to the parent structure is heterocyclyl; its non-limiting examples include:

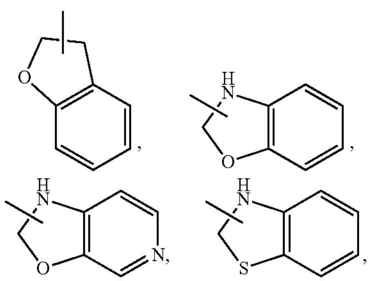

etc.

The heterocyclyl may be optionally substituted or unsubstituted, and when it is substituted, the substituent is preferably one or more groups independently selected from the group consisting of alkyl, alkenyl, alkynyl, alkoxy, alkylthio, alkylamino, halogen, sulfhydryl, hydroxy, nitro, cyano, cycloalkyl, heterocycloalkyl, aryl, heteroaryl, cycloalkoxy, heterocycloalkoxy, cycloalkylthio, heterocycloalkylthio, oxo, carboxyl and a carboxylate group.

The term "aryl" refers to a 6- to 14-membered, preferably 6- to 10-membered all-carbon monocyclic or fused polycyclic (i.e., rings that share a pair of adjacent carbon atoms) group having a conjugated π-electron system, such as phenyl and naphthyl. The aryl ring may be fused to a heteroaryl, heterocyclyl or cycloalkyl ring, wherein the ring attached to the parent structure is the aryl ring; its non-limiting examples include:

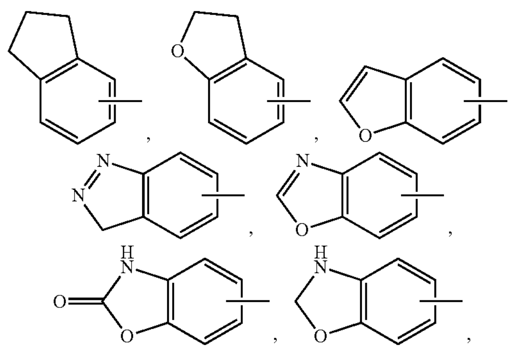

-continued

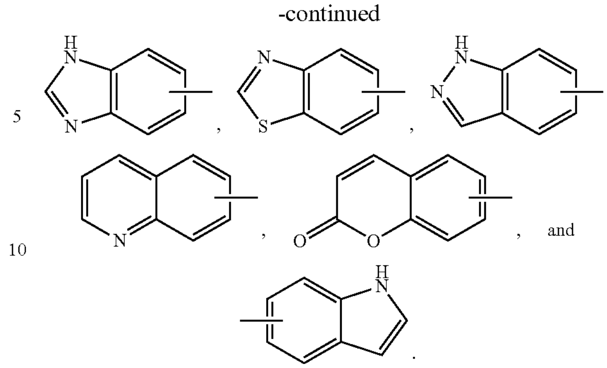

The aryl may be substituted or unsubstituted, and when it is substituted, the substituent is preferably one or more groups independently selected from the group consisting of alkyl, alkenyl, alkynyl, alkoxy, alkylthio, alkylamino, halogen, sulfhydryl, hydroxy, nitro, cyano, cycloalkyl, heterocycloalkyl, aryl, heteroaryl, cycloalkoxy, heterocycloalkoxy, cycloalkylthio, heterocycloalkylthio, carboxyl and a carboxylate group, preferably phenyl.

The term "fused cycloaryl" may be an unsaturated aromatic fused ring structure containing 8-14 ring atoms, preferably 8-12 ring atoms, formed by connecting two or more ring structures that share two adjacent atoms with each other, for example, including all unsaturated fused cycloaryl groups such as naphthalene, phenanthrene, etc., and partially saturated fused cycloaryl groups such as benzo 3- to 8-membered saturated monocyclic cycloalkyl, benzo 3- to 8-membered partially saturated monocyclic cycloalkyl, specifically, 2,3-dihydro-1H-indenyl, 1H-indenyl, 1,2,3,4-tetrahydronaphthyl, 1,4-dihydronaphthyl, and the like.

The term "heteroaryl" refers to a heteroaromatic system containing 1 to 4 heteroatoms and 5 to 14 ring atoms, wherein the heteroatoms are selected from the group consisting of oxygen, sulfur and nitrogen. The heteroaryl is preferably 5- to 12-membered, e.g., imidazolyl, furyl, thienyl, thiazolyl, pyrazolyl, oxazolyl, pyrrolyl, tetrazolyl, pyridyl, pyrimidinyl, thiadiazole, pyrazinyl, and the like, preferably imidazolyl, pyrazolyl, pyrimidinyl or thiazolyl; and more preferably pyrazolyl or thiazolyl. The heteroaryl ring may be fused to an aryl, heterocyclyl or cycloalkyl ring, wherein the ring attached to the parent structure is the heteroaryl ring; its non-limiting examples include:

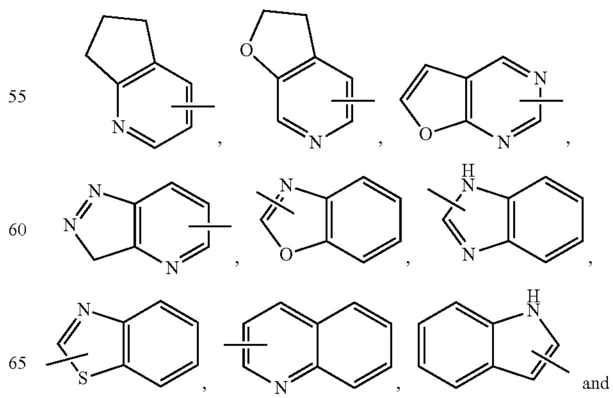

-continued

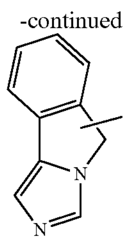

The heteroaryl may be optionally substituted or unsubstituted, and when it is substituted, the substituent is preferably one or more groups independently selected from the group consisting of alkyl, alkenyl, alkynyl, alkoxy, alkylthio, alkylamino, halogen, sulfhydryl, hydroxy, nitro, cyano, cycloalkyl, heterocycloalkyl, aryl, heteroaryl, cycloalkoxy, heterocycloalkoxy, cycloalkylthio, heterocycloalkylthio, carboxyl and a carboxylate group.

The term "fused heteroaryl" may be an unsaturated aromatic fused ring structure containing 5-14 ring atoms (at least one heteroatom) formed by connecting two or more ring structures that share two adjacent atoms with each other, including the case where a carbon atom, a nitrogen atom and a sulfur atom may be oxidized, preferably "5- to 12-membered fused heteroaryl", "7- to 12-membered fused heteroaryl", "9- to 12-membered fused heteroaryl", and the like, for example, benzofuranyl, benzoisothiafuranyl, benzothienyl, indolyl, isoindolyl, benzoxazolyl, benzimidazolyl, indazolyl, benzotriazolyl, quinolyl, 2-quinolinone, 4-quinolinone, 1-isoquinolinone, isoquinolinyl, acridinyl, phenanthridinyl, benzopyridazinyl, phthalazinyl, quinazolinyl, quinoxalinyl, phenazinyl, pteridinyl, purinyl, naphthyridinyl, phenazine, phenothiazine, and the like.

The fused heteroaryl may be optionally substituted or unsubstituted, and when it is substituted, the substituent is preferably one or more groups independently selected from the group consisting of alkyl, alkenyl, alkynyl, alkoxy, alkylthio, alkylamino, halogen, sulfhydryl, hydroxy, nitro, cyano, cycloalkyl, heterocycloalkyl, aryl, heteroaryl, cycloalkoxy, heterocycloalkoxy, cycloalkylthio, heterocycloalkylthio, carboxyl and a carboxylate group.

The term "alkoxy" refers to —O-(alkyl) and —O-(unsubstituted cycloalkyl), wherein the alkyl is as defined above. Non-limiting examples of alkoxy include: methoxy, ethoxy, propoxy, butoxy, cyclopropyloxy, cyclobutoxy, cyclopentyloxy and cyclohexyloxy. The alkoxy may be optionally substituted or unsubstituted, and when it is substituted, the substituent is preferably one or more groups independently selected from the group consisting of alkyl, alkenyl, alkynyl, alkoxy, alkylthio, alkylamino, halogen, sulfhydryl, hydroxy, nitro, cyano, cycloalkyl, heterocycloalkyl, aryl, heteroaryl, cycloalkoxy, heterocycloalkoxy, cycloalkylthio, heterocycloalkylthio, carboxyl and a carboxylate group.

The term "alkylthio" refers to —S-(alkyl) and —S-(unsubstituted cycloalkyl), wherein the alkyl is as defined above. Non-limiting examples of alkylthio include: methylthio, ethylthio, propylthio, butylthio, cyclopropylthio, cyclobutylthio, cyclopentylthio and cyclohexylthio. The alkylthio may be optionally substituted or unsubstituted, and when it is substituted, the substituent is preferably one or more of the following groups; it is substituted with one or more substituents independently selected from the group consisting of alkyl, alkenyl, alkynyl, alkoxy, alkylthio, alkylamino, halogen, sulfhydryl, hydroxy, nitro, cyano, cycloalkyl, heterocycloalkyl, aryl, heteroaryl, cycloalkoxy, heterocycloalkoxy, cycloalkylthio and heterocycloalkylthio.

The term "hydroxyalkyl" refers to an alkyl group substituted with hydroxy, wherein the alkyl is defined as above.

The term "haloalkyl" refers to an alkyl group substituted with halogen, wherein the alkyl group is as defined above.

The term "deuterated alkyl" refers to an alkyl group substituted with a deuterium atom, wherein the alkyl group is as defined above.

The term "hydroxy" refers to the —OH group.

The term "oxo" refers to the =O group. For example, a carbon atom is connected to an oxygen atom via a double bond to form a ketone or aldehyde group.

The term "thio" refers to the =S group. For example, the carbon atom is connected to a sulfur atom via a double bond to form thiocarbonyl-C(S)—.

The term "halogen" refers to fluorine, chlorine, bromine, or iodine.

The term "amino" refers to $—NH_2$.

The term "cyano" refers to —CN.

The term "nitro" refers to $—NO_2$.

The term "carboxyl" refers to —C(O)OH.

The term "aldehyde" refers to —CHO.

The term "carboxylate group" refers to —C(O)O(alkyl) or —C(O)O(cycloalkyl), wherein the alkyl and cycloalkyl are as defined above.

The term "acyl halide" refers to a compound containing a —C(O)-halogen group.

The "carboxyl protecting group" is a suitable group known in the art for carboxyl protection; see the literature ("Protective Groups in Organic Synthesis", $5^{Th}$ Ed. T. W. Greene & P. G. M. Wuts) for the carboxyl protecting groups. By way of example, preferably, the carboxyl protecting group may be a substituted or unsubstituted $C_{1-10}$ linear or branched alkyl, substituted or unsubstituted $C_{2-10}$ linear or branched alkenyl or alkynyl, substituted or unsubstituted $C_{3-8}$ cyclic alkyl, substituted or unsubstituted $C_{5-10}$ aryl or heteroaryl, or $(C_{1-8}$ alkyl or aryl$)_3$ silyl; preferably $C_{1-6}$ linear or branched alkyl, and more preferably $C_{1-4}$ linear or branched alkyl. For example, the carboxyl protecting group may be methyl, ethyl, allyl, isopentenyl, trimethylsilylethyl, or the like.

The term "amino protecting group" is a suitable group known in the art for amino protection; see the literature ("Protective Groups in Organic Synthesis", $5^{Th}$. Ed. T. W. Greene & P. G. M. Wuts) for the amino protecting groups. Preferably, the amino protecting group may be ($C_{1-10}$ alkyl or aryl)acyl, e.g., formyl, acetyl, benzoyl, or the like; ($C_{1-6}$ alkyl or $C_{6-10}$ aryl)sulfonyl; ($C_{1-6}$ alkoxy or $C_{6-10}$ aryloxy) carbonyl, e.g., Boc or Cbz; or substituted or unsubstituted alkyl, e.g., trityl (Tr), 2,4-dimethoxybenzyl (DMB), p-methoxybenzyl (PMB) or benzyl (Bn).

The "hydroxy protecting group" is a suitable group known in the art for hydroxy protection; see the literature ("Protective Groups in Organic Synthesis", $5^{Th}$ Ed. T. W. Greene & P. G. M. Wuts) for the hydroxy protecting groups. By way of example, preferably, the hydroxy protecting group may be $(C_{1-10}$alkyl or aryl$)_3$silyl, e.g., triethylsilyl, triisopropylsilyl, tert-butyldimethylsilyl, tert-butyldiphenylsilyl, or the like; $C_{1-10}$ alkyl or substituted alkyl, preferably alkoxy or aryl-substituted alkyl, and more preferably $C_{1-6}$ alkoxy-substituted $C_{1-6}$ alkyl or phenyl-substituted $C_{1-6}$ alkyl, and most preferably $C_{1-4}$ alkoxy-substituted $C_{1-4}$ alkyl, e.g., methyl, tert-butyl, allyl, benzyl, methoxymethyl (MOM), ethoxyethyl, 2-tetrahydropyranyl (THP), or the like; ($C_{1-10}$ alkyl or aryl)acyl, e.g., formyl, acetyl, benzoyl, or the like; ($C_{1-6}$ alkyl or $C_{6-10}$ aryl)sulfonyl; or ($C_{1-6}$ alkoxy or $C_{6-10}$ aryloxy)carbonyl.

The term "leaving group" refers to an atom or a functional group that is detached from a larger molecule in a chemical reaction. Representative leaving groups include halogen, substituted sulfonyloxy, phosphoryloxy, amino, $R_iR_jN$—, cyano, $R_mS$—, and the like.

The substituted sulfonyloxy may be $C_1$-$C_6$ alkylsulfonyloxy, perfluoro $C_1$-$C_6$ alkylsulfonyloxy, arylsulfonyloxy, aralkylsulfonyloxy, or the like.

Specific examples of the $C_1$-$C_6$ alkylsulfonyloxy include $C_1$-$C_6$ linear or branched alkylsulfonyloxy, e.g., methylsulfonyloxy, ethylsulfonyloxy, n-propylsulfonyloxy, isopropylsulfonyloxy, n-butylsulfonyloxy, tert-butylsulfonyloxy, n-pentylsulfonyloxy and n-hexylsulfonyloxy.

Specific examples of perfluoro $C_1$-$C_6$ alkylsulfonyloxy include $C_1$-$C_6$ linear or branched perfluoroalkylsulfonyloxy, e.g., trifluoromethylsulfonyloxy, 1,1,2,2,2-pentafluoro-1-ethylsulfonyloxy, 1,1,2,2,3,3,3-heptafluoro-1-propylsulfonyloxy, and 1,1,2,2,3,3,4,4,4-nonafluoro-1-butylsulfonyloxy.

Examples of arylsulfonyloxy include: phenylsulfonyloxy and naphthylsulfonyloxy optionally having 1 to 3 substituents on the phenyl ring selected from the group consisting of $C_1$-$C_6$ linear or branched alkyl, $C_1$-$C_6$ linear or branched alkyl, nitro and halogen atoms. Specific examples of the phenylsulfonyloxy having a substituent include phenylsulfonyloxy, 4-methylphenylsulfonyloxy, 2-methylphenylsulfonyloxy, 4-nitrophenylsulfonyloxy, 4-tolylsulfonyloxy, 2-nitrophenylsulfonyloxy, 3-chlorophenylsulfonyloxy, and the like. Specific examples of naphthylsulfonyloxy include α-naphthylsulfonyloxy, β-naphthylsulfonyloxy, and the like.

Examples of aralkylsulfonyloxy include: $C_1$-$C_6$ linear or branched alkylsulfonyloxy substituted with phenyl (which optionally has 1 to 3 substituents on the phenyl ring selected from the group consisting of $C_1$-$C_6$ linear or branched alkyl, $C_1$-$C_6$ linear or branched alkyl, nitro and halogen atoms); and $C_1$-$C_6$ linear or branched alkylsulfonyloxy substituted with naphthyl. Specific examples of the alkylsulfonyloxy substituted with phenyl include benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methylbenzylsulfonyloxy, 3-chlorobenzylsulfonyloxy, and the like. Specific examples of the alkylsulfonyloxy substituted with naphthyl include α-naphthylmethylsulfonyloxy, β-naphthylmethylsulfonyloxy, and the like.

"Optional" or "optionally" means that the event or circumstance subsequently described may, but does not necessarily, occur, and that the description includes instances where the event or circumstance occurs or does not occur. For example, "a heterocyclyl group optionally substituted with alkyl" means that the alkyl may, but does not necessarily, exist, and that the description includes instances where the heterocyclyl group is or is not substituted with the alkyl.

"Substituted" means that one or more, preferably up to 5, more preferably 1 to 3 hydrogen atoms in the group are independently substituted with a corresponding number of substituents. It goes without saying that a substituent is only in its possible chemical position, and those skilled in the art will be able to determine (experimentally or theoretically) possible or impossible substitution without undue effort.

In the chemical structure of the compound described herein, a "⟋" bond is not specified with a configuration, that is, a "⟋" bond may be "⋰" or "◢", or includes both "⋰" and "◢" configurations. In the chemical structure of the compound described herein, a bond "⫽" is not specified with a configuration, that is, it may be in a Z configuration or an E configuration, or contains both configurations.

Tautomers are structural isomers of organic compounds that readily interconvert by a chemical reaction called tautomerization. This reaction often results in the formal migration of hydrogen atoms or protons accompanied by the conversion of a single bond to an adjacent double bond. Some common tautomeric pairs include: keto-enol and lactam-lactim. An example of a lactam-lactim equilibrium is present between A and B as shown below.

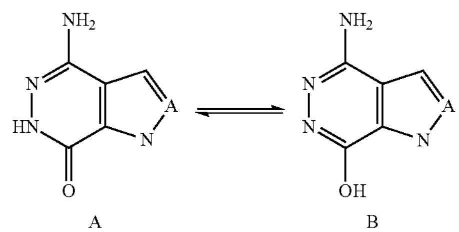

All compounds in the present disclosure can be drawn as form A or form B. All tautomeric forms are within the scope of the present disclosure. The nomenclature of the compounds does not exclude any tautomers.

Any isotopically-labeled derivative of the compound or the pharmaceutically acceptable salt thereof of the present disclosure is encompassed by the present disclosure. Atoms that can be isotopically labeled include, but are not limited to, hydrogen, carbon, nitrogen, oxygen, phosphorus, fluorine, chlorine, iodine, and the like. They may be replaced by isotopes $^{2}H(D)$, $^{3}H$, $^{11}C$, $^{13}C$, $^{14}C$, $^{15}N$, $^{18}F$, $^{31}P$, $^{32}P$, $^{35}S$, $^{36}Cl$, $^{125}I$, and the like. Unless otherwise stated, when a position is specifically designated as deuterium (D), that position shall be understood to be deuterium having an abundance that is at least 3000 times greater than the natural abundance of deuterium (which is 0.015%) (i.e., incorporating at least 45% deuterium).

DETAILED DESCRIPTION

The preparation of the compound described herein and a pharmaceutically acceptable salt thereof is further described below in conjunction with examples, which are not intended to limit the scope of the present disclosure.

Experimental procedures without conditions specified in the examples of the present disclosure are generally conducted according to conventional conditions, or according to conditions recommended by the manufacturers of the starting materials or commercial products. Reagents without specific origins indicated are commercially available conventional reagents.

The structures of the compounds were determined by nuclear magnetic resonance (NMR) spectroscopy and/or mass spectrometry (LCMS). NMR shifts (δ) were given in $10^{-6}$ (ppm). NMR analysis was performed on a Bruker AVANCE-400 nuclear magnetic resonance instrument, with deuterated dimethyl sulfoxide (DMSO-$d_6$), deuterated chloroform ($CDCl_3$) and deuterated methanol ($CD_3OD$) as solvents and tetramethylsilane (TMS) as an internal standard. The spatial configurations of the optical isomers (isomers) of the compounds can be further confirmed by determining single crystal parameters.

HPLC analysis was performed on Waters ACQUITY ultra high performance LC, Shimadzu LC-20A systems, Shimadzu LC-2010HT series, or Agilent 1200 LC high performance liquid chromatograph (ACQUITY UPLC BEH C18 1.7 μm 2.1×50 mm column, Ultimate XB-C18 3.0×150 mm column, or Xtimate C18 2.1×30 mm column).

MS analysis was performed on a Waters SQD2 mass spectrometer in the positive/negative ion scan mode with a mass scan range of 100-1200.

Chiral HPLC analysis was performed using a Chiralpak IC-3 100×4.6 mm I.D., 3 μm; Chiralpak AD-3 150×4.6 mm I.D., 3 μm; Chiralpak AD-3 50×4.6 mm I.D., 3 μm; Chiralpak AS-3 150×4.6 mm I.D., 3 μm; Chiralpak AS-3 100×4.6 mm I.D., 3 μm; ChiralCel OD-3 150×4.6 mm I.D., 3 μm; Chiralcel OD-3 100×4.6 mm I.D., 3 μm; ChiralCel OJ-H 150×4.6 mm I.D., 5 μm; or Chiralcel OJ-3 150×4.6 mm I.D., 3 μm column. Yantai Huanghai HSGF254 or Qingdao GF254 silica gel plates, 0.15-0.2 mm layer thickness, were adopted for thin-layer chromatography (TLC) analysis and 0.4-0.5 mm layer thickness for TLC separation and purification.

Flash column purification was performed on a Combiflash Rf150 (TELEDYNE ISCO) or Isolara one (Biotage) system.

Normal phase column chromatography generally used 100-200 mesh, 200-300 mesh or 300-400 mesh Yantai Huanghai silica gel as a carrier, or used a Changzhou Santai pre-fill ultrapure normal phase silica gel column (40-63 μm, 60 g, 12 g, 25 g, 40 g, 80 g or other specifications).

Reversed-phase column chromatography generally used a Changzhou Santai pre-fill ultrapure C18 silica gel column (20-45 μm, 100 Å, 40 g, 80 g, 120 g, 220 g or other specifications).

High pressure column purification was performed on a Waters AutoP system in combination with a Waters XBridge BEH C18 OBD Prep Column, 130 Å, 5 μm, 19 mm×150 mm or Atlantis T3 OBD Prep Column, 100 Å, 5 μm, 19 mm×150 mm. Preparative chiral chromatography used a DAICEL CHIRALPAK IC (250 mm×30 mm, 10 μm) or Phenomenex-Amylose-1 (250 mm×30 mm, 5 μm) column.

Known starting materials in the present disclosure may be synthesized using or according to methods known in the art, or may be purchased from Shanghai Titan Scientific, ABCR GmbH & Co. KG, Acros Organics, Aldrich Chemical Company, Accela ChemBio Inc., Darui Chemicals, and other companies.

In the example, all reactions can be performed under nitrogen atmosphere unless otherwise specified.

The argon atmosphere or nitrogen atmosphere means that the reaction flask is connected to a balloon containing about 1 L of argon or nitrogen.

The hydrogen atmosphere means that the reaction flask is connected to a balloon containing about 1 L of hydrogen.

Pressurized hydrogenation reactions were performed using a Parr 3916EKX hydrogenator and a Qinglan QL-500 hydrogenator, or an HC2-SS hydrogenator.

Hydrogenation reactions generally involve 3 cycles of vacuumization and hydrogen purging.

Microwave reactions were performed on a CEM Discover-S 908860 microwave reactor.

In the examples, a solution refers to an aqueous solution unless otherwise specified.

In the examples, the reaction temperature refers to room temperature, i.e., 20° C. to 30° C., unless otherwise specified.

The reaction progress in the examples is monitored by thin-layer chromatography (TLC). The developing solvent for reactions, the eluent system for column chromatography purification and the developing solvent system for thin-layer chromatography include: A: dichloromethane/methanol system, B: n-hexane/ethyl acetate system, C: petroleum ether/ethyl acetate system, D: petroleum ether/ethyl acetate/methanol system, and E: petroleum ether/tetrahydrofuran system. The volume ratio of the solvents is adjusted according to the polarity of the compound, or by adding a small amount of basic or acidic reagents such as triethylamine and acetic acid.

Example 1

1

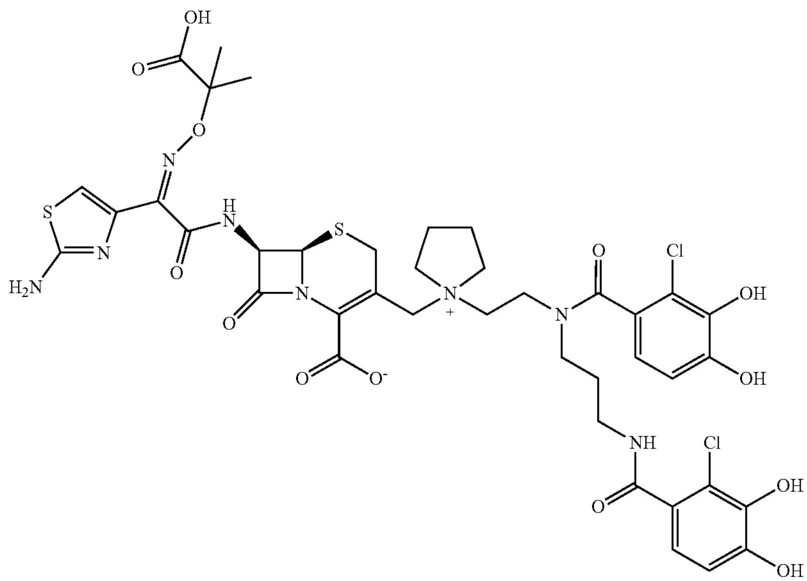

-continued
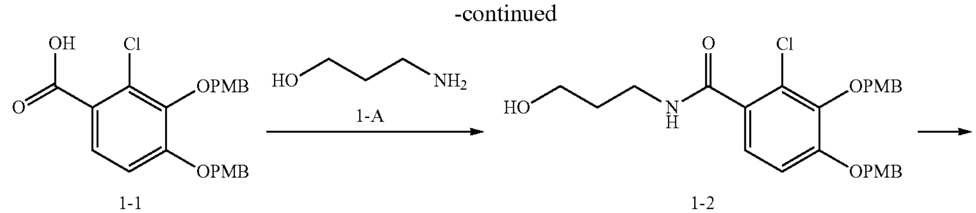
1-1
1-2
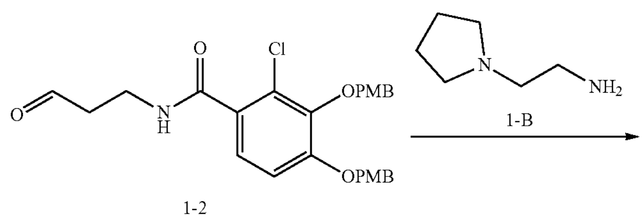
1-2
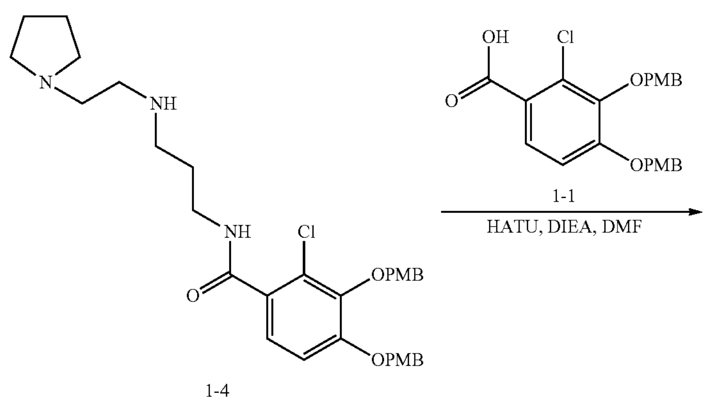
1-4
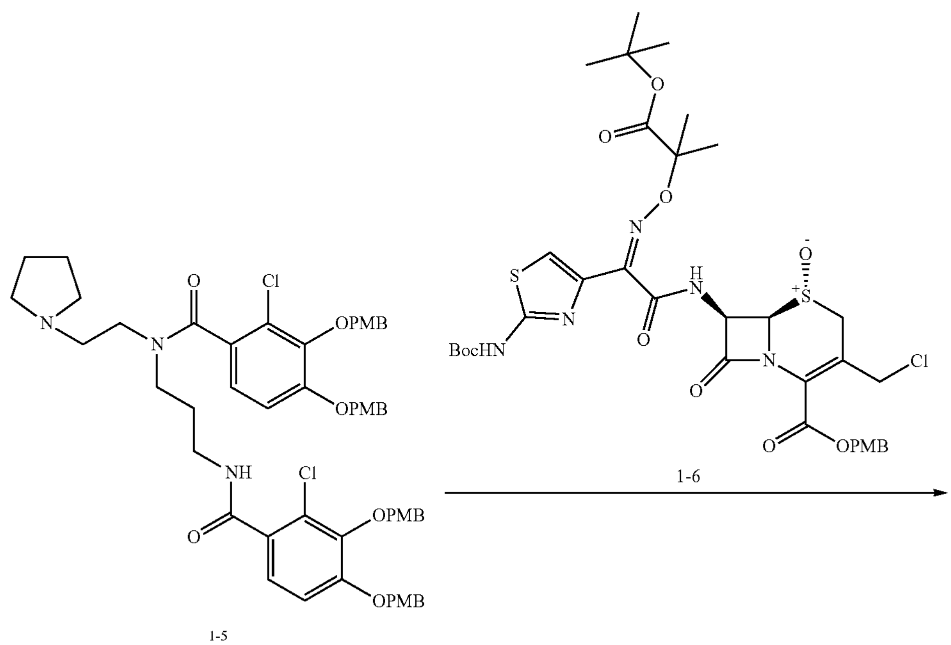
1-5

-continued

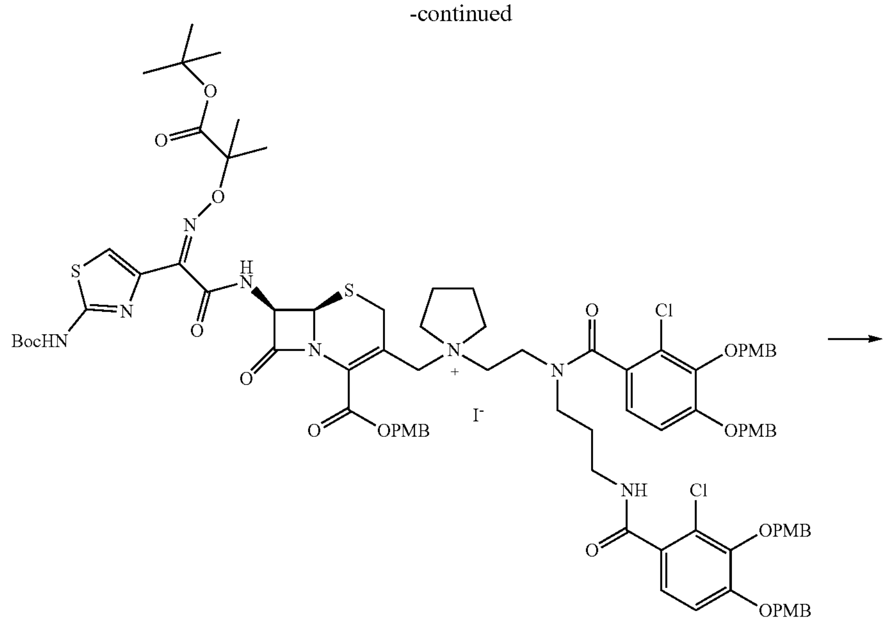

1-7

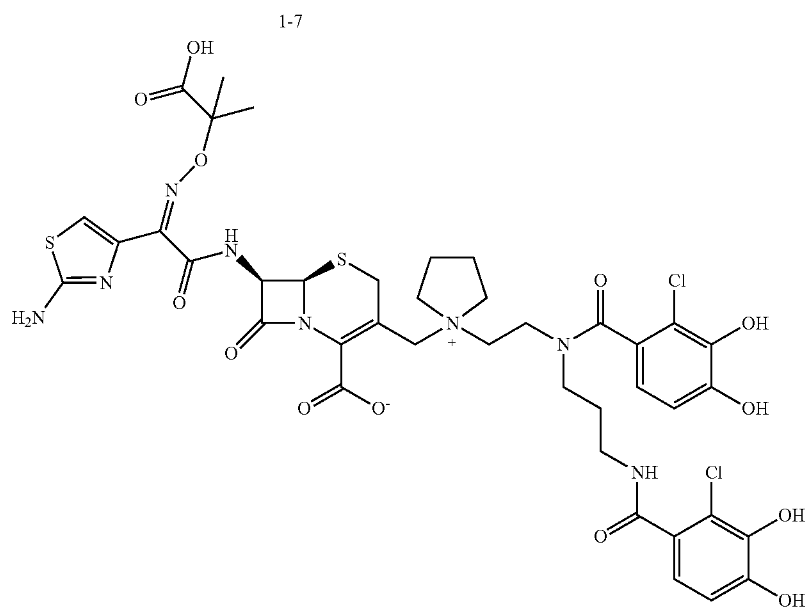

1

Step 1

To a solution of compound 1-1 (synthesized according to the method of the patent CN106661052A, 1.5 g, 3.50 mmol) in DMF (35 mL) were added DMTMM (1.55 g, 5.26 mmol) and DIEA (905 mg, 7.0 mmol). After the reaction was purged with argon three times, 1-A (525 mg, 7.0 mmol) was added to the above reaction mixture, and the reaction was then stirred at room temperature for 2 h. The reaction mixture was slowly added to water, and a solid product gradually precipitated. The solid product obtained by filtration was dissolved in DCM. The solution was extracted, and the organic phase was separated, washed with water and then with saturated brine, dried over anhydrous sodium sulfate, filtered and evaporated to dryness to give the product 1-2 (1.6 g, yield: 94%).

LC/MS (ESI): m/z 486.1 $[M+H]^+$

Step 2

A solution of oxalyl chloride (1.05 g, 8.24 mmol) in DCM (10 mL) was cooled to −78° C. in a dry ice/acetone bath, and DMSO (1.29 g, 16.5 mmol) was added dropwise under argon atmosphere. The reaction was then stirred. A solution of 1-2 (1.6 g, 3.30 mmol) in DCM (6 mL) was added slowly dropwise to the above reaction mixture, and the mixture was stirred at −78° C. $Et_3N$ (3.34 g, 33.0 mmol) was added, and the mixture was stirred at −78° C. The reaction was then slowly warmed to 0° C. and was completed. The reaction mixture was quenched with $H_2O$ and then extracted with DCM. The organic phase was washed with water and then with saturated brine, dried over anhydrous sodium sulfate, filtered and evaporated to dryness to give a crude product. The crude product was purified by flash chromatography on silica gel to give the product 1-3 (1.28 g, yield: 80%).

LC/MS (ESI): m/z 484.0 $[M+H]^+$

Step 3

To a solution of substrate 1-3 (1.28 g, 2.65 mmol) in DCM (26 mL) was added 1-B (605 mg, 5.30 mmol). After the reaction mixture was cooled in an ice-water bath, NaBH$(OAc)_3$ (1.68 g, 7.95 mmol) was added. The reaction was warmed to room temperature and stirred. After the reaction was complete, the reaction mixture was quenched with $NaHCO_3$ solution and then extracted with DCM. The organic phase was washed with water and then with saturated brine, dried over anhydrous sodium sulfate, filtered and evaporated to dryness to give a crude product. The crude product was purified by flash chromatography on silica gel to give the product 1-4 (735 mg, yield: 48%).

LC/MS (ESI): m/z 582.1 $[M+H]^+$

Step 4

To a solution of 1-1 (650 mg, 1.51 mmol) in DMF (13 mL) were added HATU (961 mg, 2.52 mmol) and DIEA (490 mg, 3.78 mmol). The reaction was stirred at room temperature under argon atmosphere. 1-4 (735 mg, 1.26 mmol) was added to the above reaction mixture, and the reaction was then stirred at room temperature. The reaction mixture was slowly added to water, filtered and dried in vacuo to give the product 1-5 (1.2 g, yield: 96%).

LC/MS (ESI): m/z 992.1 $[M+H]^+$

Step 5

Compound 1-5 (546 mg, 0.55 mmol), compound 1-6 (synthesized according to the method of the patent WO2016035847, 398 mg, 0.5 mmol) and sodium iodide (225 mg, 1.5 mmol) were added to N,N-dimethylformamide (1.5 mL), and the reaction was stirred. After the reaction was complete, the reaction flask was cooled in an ice-water bath. $PBr_3$ (360 mg, 1.33 mmol) was added, and the reaction was stirred. After the reaction was complete, the reaction mixture was added dropwise to aqueous $NaHSO_3$ solution and filtered, and the filter cake was washed with clear water and dried in vacuo to give crude 1-7 (1.13 g).

LC/MS (ESI): m/z 1737.1 $[M]^+$

Step 6

Compound 1-7 (1.13 g, 0.5 mmol) was added to anisole (2 mL) and trifluoroacetic acid (8 mL), and the mixture was allowed to react at room temperature. Methyl tert-butyl ether was added, and the mixture was stirred and then filtered. The filter cake was rinsed with MTBE and then dried to give a crude product (600 mg). The crude product was purified by preparative HPLC to give compound 1 (4 mg).

HRMS: 979.1874 $[M+H]^+$ $^1$H-NMR (400 MHz, DMSO-$d_6$) δ: 1.44 (s, 3H), 1.46 (s, 3H), 1.66-2.06 (m, 6H), 2.93-3.88 (m, 14H), 3.04-3.05 (m, 2H), 4.00-4.03 (m, 2H), 4.82-5.13 (m, 1H), 5.18 (d, 1H), 5.74 (dd, 1H), 6.54 (d, 1H), 6.60 (d, 1H), 6.73-6.85 (m, 3H), 7.28 (s, 2H), 8.05-8.33 (m, 1H), 9.46 (br s, 2H), 10.26 (br s, 2H).

Example 2

2

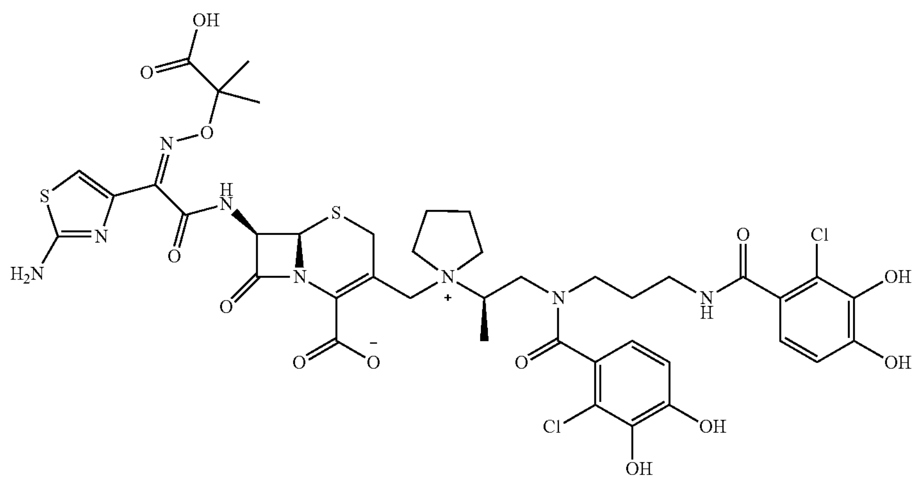

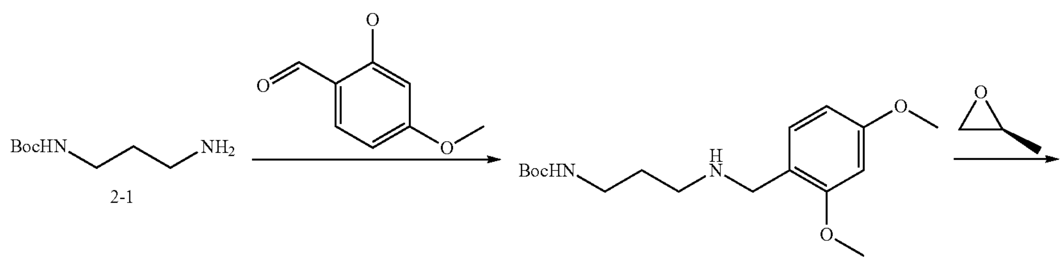

2-1

2-2

-continued
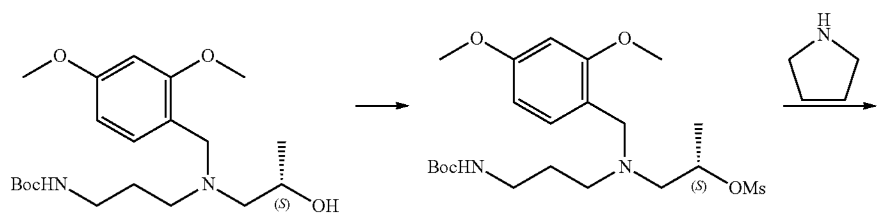
2-3
2-4
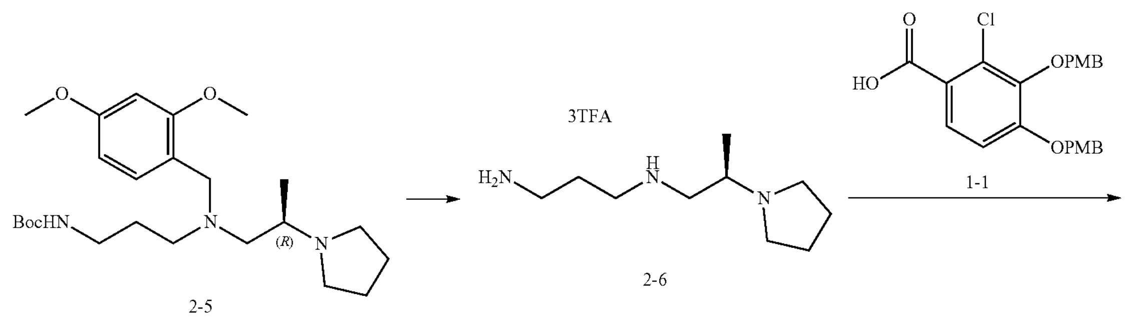
3TFA
1-1
2-5
2-6
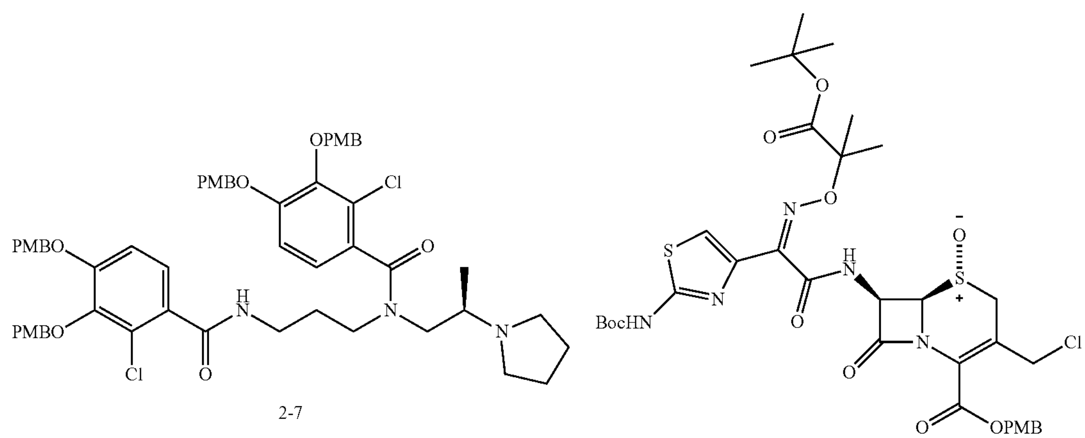
2-7
1-6
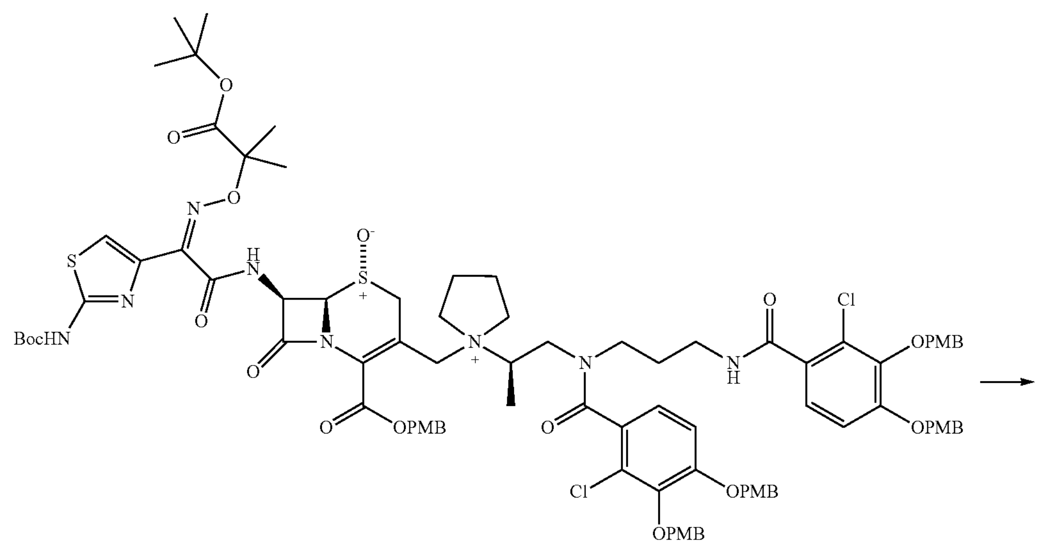
2-8

-continued

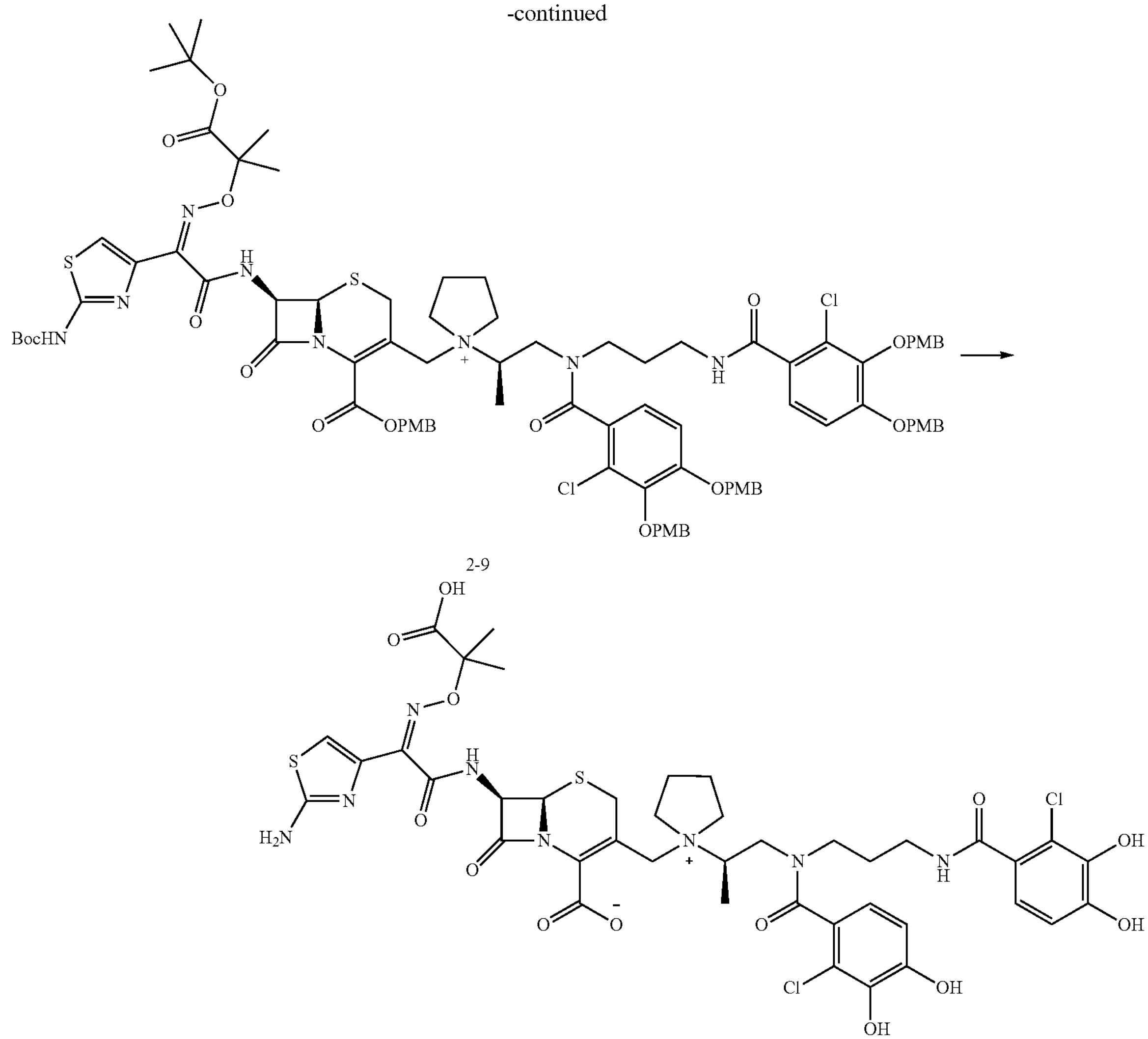

2-9

2

Step 1

To a reaction flask were added 2-1 (30.3 g, 174.1 mmol, 1.0 eq), 2,4-dimethoxybenzaldehyde (29.5 g, 177.6 mmol, 1.02 eq), methanol (300 mL) and anhydrous sodium sulfate (24.7 g, 174.1 mmol, 1.0 eq), and the reaction was stirred at room temperature. The reaction mixture was then cooled in an ice-water bath, and sodium borohydride (3.3 g, 87.0 mmol, 0.5 eq.) was added in portions. The reaction was stirred for 5 min and then stirred at room temperature until it was complete. Acetic acid (3.3 mL) was added, and the mixture was stirred, filtered and washed with ethyl acetate. The filtrate was concentrated, and the residue was mixed with water and ethyl acetate and stirred. The aqueous phase was separated and extracted with ethyl acetate. The organic phases were combined, washed with saturated brine, dried over anhydrous sodium sulfate, filtered and concentrated to give the product 2-2 (58.0 g, yield: 102.8%).

MS m/z 325.1 $[M+H]^+$

Step 2

2-2 (2.0 g, 6.2 mmol, 1.0 eq), S-propylene oxide (0.54 g, 9.3 mmol, 1.5 eq) and EtOH (20 mL) were added to a reaction flask, and the reaction was heated to 60° C. LC-MS monitoring showed that the starting material was consumed completely. The reaction mixture was concentrated, and the crude product was purified by column chromatography to give the product 2-3 (1.2 g, yield: 51.1%).

MS m/z 383.2 $[M+H]^+$

Step 3

2-3 (1.2 g, 3.2 mmol, 1.0 eq), DCM (20 mL) and TEA (0.65 g, 6.4 mmol, 2.0 eq) were added to a reaction flask and cooled in an ice-water bath. MsCl (0.54 g, 4.7 mmol, 1.5 eq) was slowly added dropwise, and the reaction was stirred. LC-MS monitoring showed that the starting material was consumed completely. The reaction mixture was washed with water and saturated sodium chloride solution, dried over anhydrous sodium sulfate and concentrated to give crude 2-4 (1.34 g). The crude product was directly used in the next step.

MS m/z 461.1 $[M+H]^+$

Step 4

The crude 2-4 (1.34 g, 3.2 mmol, 1.0 eq), tetrahydropyrrole (0.56 g, 8.0 mmol, 2.5 eq), MeCN (15 mL) and potassium carbonate (0.66 g, 4.8 mmol, 1.5 eq) were added to a reaction flask, and the reaction was heated to 40° C. and stirred. LC-MS monitoring showed that the starting material was consumed completely. The reaction mixture was mixed with water (30 mL) and EA (30 mL) and stirred. The aqueous phase was separated and washed with EA. The organic phases were combined, washed with saturated sodium chloride solution, dried over anhydrous sodium sulfate and concentrated. The crude product was purified by column chromatography to give 2-5 (0.66 g, yield over two steps: 48.5%).

MS m/z 436.1 $[M+H]^+$

Step 5

2-5 (600 mg, 1.38 mmol) and TFA (10 mL) were added to a reaction flask, and the compound was dissolved. The reaction was heated to 60° C. and completed. The reaction mixture was concentrated to dryness and triturated with MTBE (10 mL). The supernatant was removed, and the resulting oil 2-6 was concentrated in vacuo to remove most of the solvent and directly used in the next step.

MS m/z 186.1 $[M+H]^+$

Step 6

The crude 2-6 and 1-1 (1.31 g, 3.05 mmol) were dissolved in DCM (15 mL), and the solution was stirred at 0° C. DIPEA (2.02 mL, 12.22 mmol) and HATU (1.39 g, 3.67 mmol) were added. The reaction mixture was naturally warmed to room temperature and was allowed to react until the reaction was complete. Water (10 mL) was added, and the organic phase was separated, washed with water, dried over anhydrous sodium sulfate, filtered and concentrated to dryness. The crude product was separated by column chromatography (DCM:MeOH=10:1) to give 2-7 (0.85 g).

MS m/z 1006.3 $[M+H]^+$

Step 7

1-6 (720 mg, 0.904 mmol), 2-7 (650 mg, 0.645 mmol), sodium iodide (0.406 g, 2.71 mmol) and boric acid (17 mg, 0.271 mmol) were added to a reaction flask. After the flask was purged with argon three times, NMP (2.1 mL) was added. The reaction mixture was allowed to react at room temperature until the reaction was complete. The reaction mixture was directly used in the next step without treatment.

MS m/z 1767.5 $[M]^+$

Step 8

NMP (0.7 mL) was added to the above reaction mixture, and the reaction mixture was cooled to 0° C. After phosphorus trichloride (0.103 mL, 1.17 mmol) was added, the mixture was allowed to react at 0° C. until the reaction was complete. The reaction mixture was triturated with 5% aqueous sodium hydrogen sulfite solution (20 mL) in an ice-water bath and filtered. After the filter cake was dissolved with DCM (20 mL), the solution was dried over anhydrous sodium sulfate, filtered and concentrated to dryness to give 2-9 (1.21 g).

MS m/z 1751.4 $[M]^+$

Step 9

2-9 (1.21 g, 0.69 mmol) was dissolved in anisole (0.2 mL) and trifluoroacetic acid (0.8 mL), and the solution was allowed to react at room temperature until the reaction was complete. The reaction mixture was cooled to 0° C., then triturated with MTBE (20 mL) in an ice-water bath and filtered. The filter cake was rinsed with MTBE and dried to give a crude product (0.82 g). The crude product was purified by reversed-phase preparative HPLC to give compound 2 (107 mg).

MS m/z 993.1 $[M+H]^+$

Example 3

3

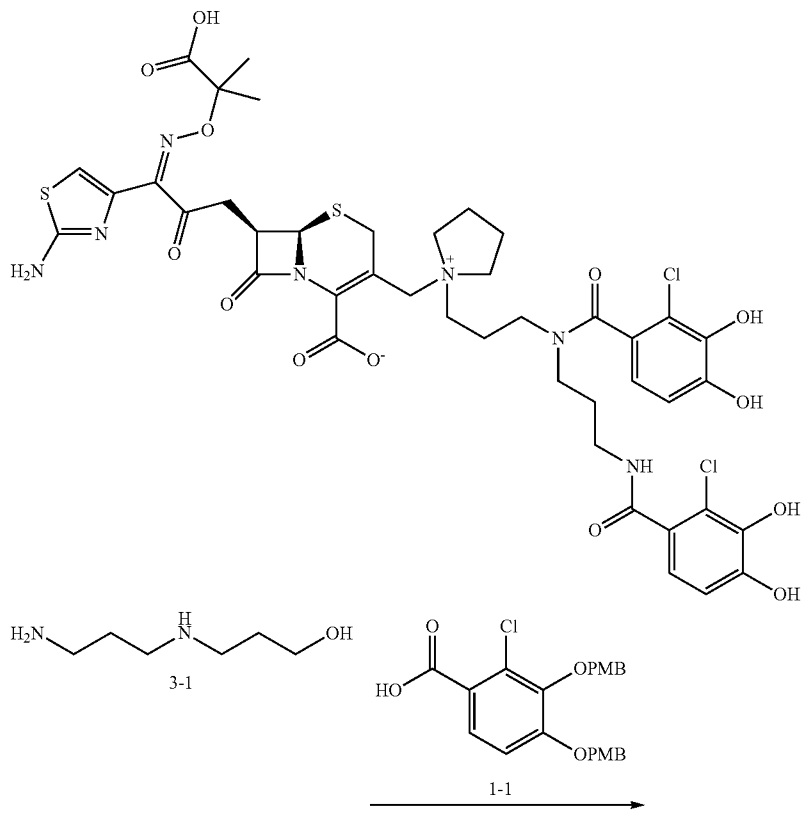

3-1

1-1

-continued
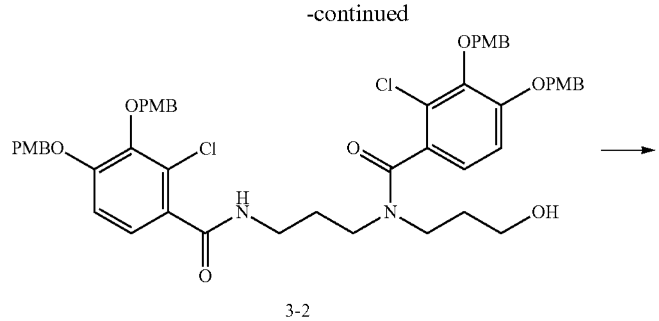
3-2
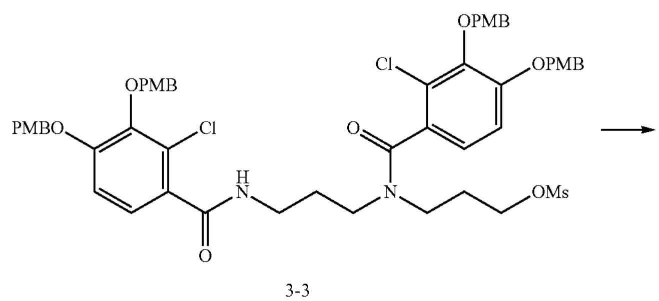
3-3
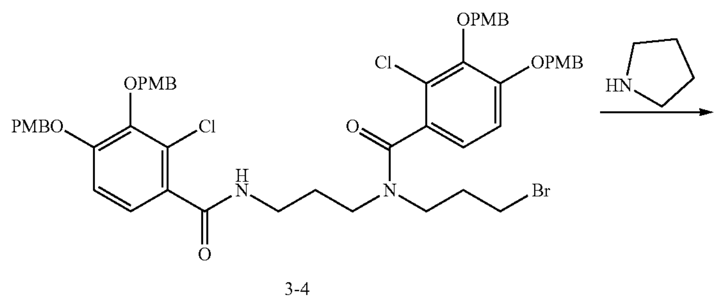
3-4
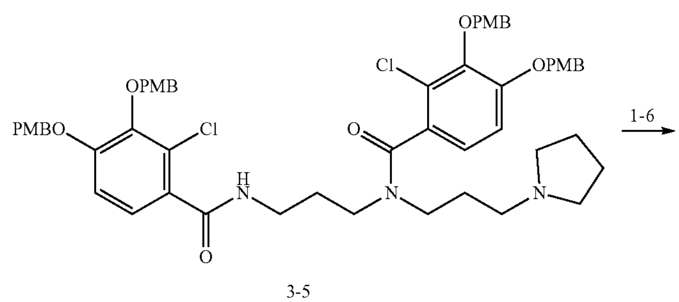
3-5

-continued
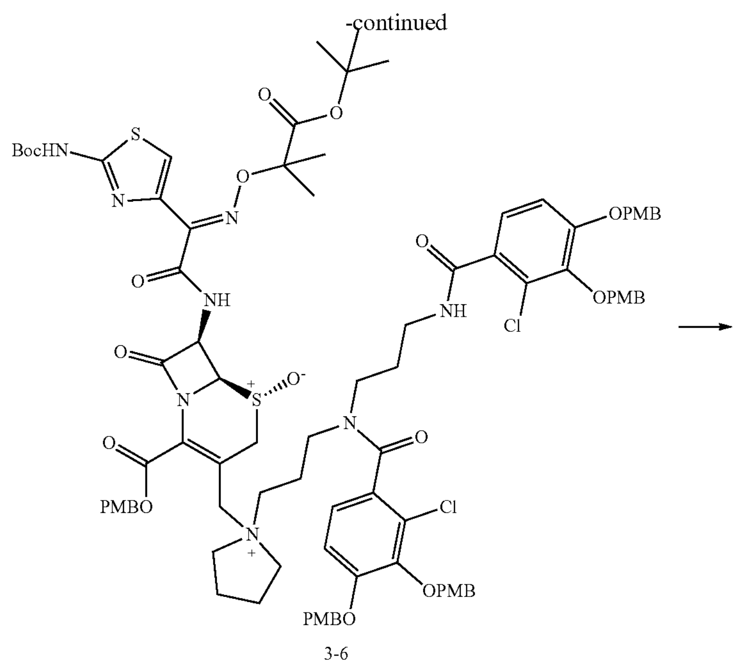
3-6
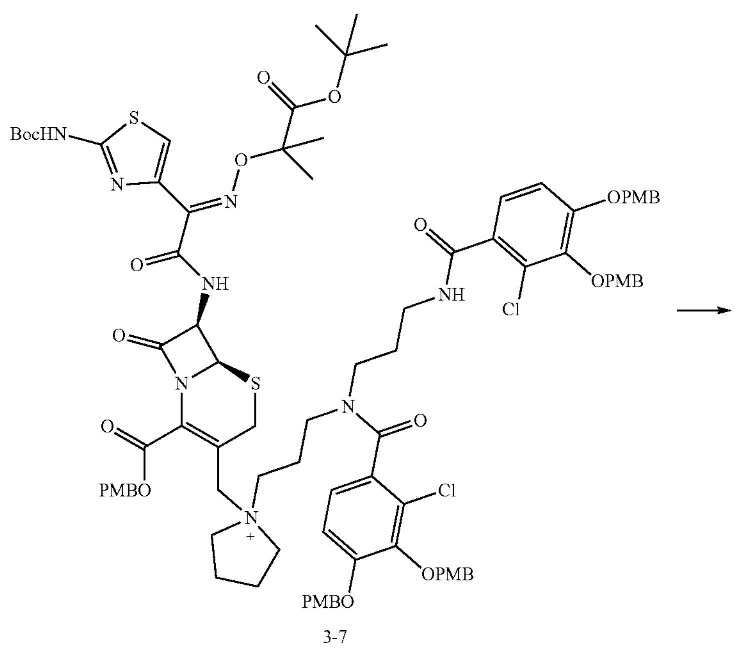
3-7

-continued

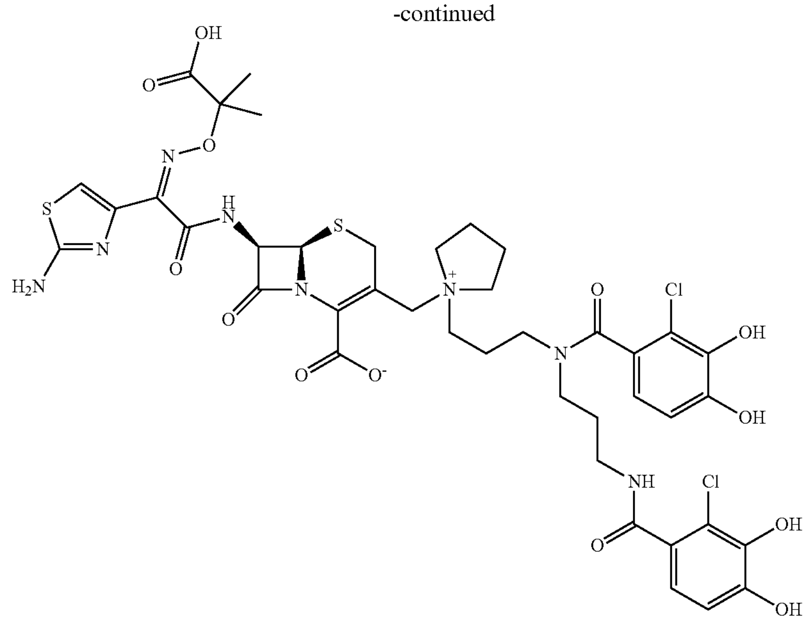

3

Step 1

To a reaction flask were added 3-1 (3.7 g, 28.0 mmol) (synthesized according to the method of Angewandte Chemie International Edition, 2010, 49, 7208-7212), 1-1 (26.4 g, 61.6 mmol) and DCM (316 mL), and the compounds were dissolved by stirring. The solution was cooled in an ice-water bath. DIPEA (11.9 g, 92.4 mmol) and DMTMM (23.2 g, 84.0 mmol) were added. The mixture was warmed to room temperature and stirred until the reaction was complete. The reaction mixture was filtered, and the filtrate was washed with water, dried over anhydrous sodium sulfate, filtered and concentrated to dryness. The crude product was purified by flash chromatography on silica gel to give the product 3-2 (21.8 g, yield: 82%).

LC/MS (ESI): m/z 953.1 $[M+H]^+$ $^1$H-NMR (400 MHz, $CDCl_3$) δ: 1.63-1.94 (m, 4H), 3.19-3.27 (m, 3H), 3.42-3.47 (m, 2H), 3.61-3.65 (m, 1H), 3.67-3.82 (m, 14H), 3.90-3.97 (m, 1H), 4.88-5.04 (m, 8H), 6.77-6.97 (m, 12H), 7.22-7.40 (m, 8H).

Step 2

3-2 (21.7 g, 22.75 mmol) and DCM (217 mL) were added to a reaction flask. The flask was purged with nitrogen and cooled in an ice-water bath. TEA (8.06 g, 79.63 mmol) was added dropwise. MsCl (7.82 g, 68.25 mmol) was dissolved in 8 mL of DCM and the solution was slowly added dropwise to the reaction system. After the addition, the mixture was stirred in an ice-water bath until the reaction was complete. The reaction was quenched with water and the pH was adjusted to 8 with saturated aqueous $NaHCO_3$ solution. The organic phase was separated and collected. The aqueous phase was extracted with DCM. The organic phases were combined, dried over anhydrous sodium sulfate, filtered and concentrated to dryness to give the product 3-3 (24.0 g, yield: 102%).

LC/MS (ESI): m/z 1031.2 $[M+H]^+$

Step 3

To a reaction flask were added 3-3 (23.9 g, 22.75 mmol) and THF (240 mL), and the compound was dissolved by stirring. LiBr (5.93 g, 68.25 mmol) was added. After the addition, the reaction was heated to 60° C. and stirred. After the reaction was complete, the reaction mixture was concentrated to remove the solvent. Water was added, and the mixture was extracted with EA. The organic phases were combined, dried over anhydrous sodium sulfate and filtered. The filtrate was concentrated to dryness to give the product 3-4 (22.2 g, yield: 94%).

LC/MS (ESI): m/z 1015.2 $[M+H]^+$

Step 4

To a reaction flask were added 3-4 (22.1 g, 21.73 mmol) and ACN (442 mL), and the compound was dissolved by stirring. $K_2CO_3$ (10.51 g, 76.06 mmol) and pyrrolidine (4.64 g, 65.19 mmol) were then added separately. After the addition, the reaction was heated to 60° C. and stirred. After the reaction was complete, the reaction mixture was concentrated to remove the solvent. Water was added, and the mixture was extracted with a mixture of the solvents DCM and MeOH (10:1). The organic phases were combined and washed with saturated brine. The organic phases were dried over anhydrous sodium sulfate, filtered and concentrated to dryness. The crude product was purified by normal phase column chromatography on silica gel to give the product 3-5 (16.2 g, yield: 74%).

LC/MS (ESI): m/z 1006.3 $[M+H]^+$ $^1$H-NMR (400 MHz, DMSO-d6) δ: 1.50-1.65 (m, 4H), 1.74-1.89 (m, 4H), 2.21-2.38 (m, 3H), 2.69-2.91 (m, 3H), 2.99-3.16 (m, 4H), 3.60-3.68 (m, 2H), 3.70-3.77 (m, 12H), 4.81-5.16 (m, 8H), 6.81-7.45 (m, 20H), 8.16-8.34 (m, 1H).

Step 5

To a reaction flask were added 1-6 (5.4 g, 6.78 mmol), 3-5 (8.2 g, 8.14 mmol), NaI (3.05 g, 20.34 mmol) and boric acid (136 mg, 2.03 mmol), and the flask was purged with argon three times. NMP (27 mL) was added under an ice-water bath. After the addition, the mixture was warmed to room temperature and stirred until the reaction was complete. The reaction mixture was directly used in the next step without further purification.

LC/MS (ESI): m/z 1767.9 $[M]^+$ (ion current of the strongest response)

Step 6

The reaction mixture from the previous step was cooled to 0° C. Phosphorus trichloride (1.58 g, 11.53 mmol) was slowly added dropwise. After the addition, the mixture was stirred at 0° C. until the reaction was complete. The reaction mixture was diluted with water and filtered to give crude 3-7 (14 g). The crude product was dried in vacuo and directly used in the next step.

LC/MS (ESI): m/z 1751.5 $[M]^+$ (ion current of the strongest response)

Step 7

The crude 3-7 was dissolved in anisole (28 mL) and trifluoroacetic acid (112 mL), and the solution was allowed to react at room temperature. After the reaction was complete, the reaction mixture was cooled to 0° C., triturated with MTBE (200 mL) in an ice-water bath and filtered. The filter cake was rinsed with MTBE and dried to give a crude product (8 g). The crude product was purified by reversed-phase preparative HPLC to give the product compound 3 (3.37 g, yield: 50%).

LC/MS (ESI): m/z 993.2 $[M+H]^+$ $^1$H-NMR (400 MHz, DMSO-d6) δ: 1.44-1.46 (m, 6H), 1.59-2.20 (m, 8H), 2.83-3.89 (m, 16H), 4.87-5.19 (m, 2H), 5.68-5.79 (m, 1H), 6.53-6.64 (m, 1H), 6.67-6.84 (m, 4H), 7.30 (s, 2H), 8.30 (s, 1H), 9.42 (br s, 3H), 10.14 (br s, 2H).

Biological Evaluation

The present disclosure is further described and explained below with reference to test examples, which are not intended to limit the scope of the present disclosure.

Test Example 1: Antifungal Activity Test

1. The test compounds were dissolved in sterile normal saline, vortexed for uniformly mixing, and diluted in a 2-fold dilution with the sterile normal saline (11 concentration points in total). The test concentration range was 32-0.031 μg/mL, and two duplicate wells were set for each concentration. Additional wells without drug dosing were set as growth controls.
2. 4 μL of the diluent was added to 196 μL of the bacterial suspension in a 96-well plate (the bacterial count in the bacterial suspension was $2\text{-}8\times10^5$ colony forming units/mL).
3. After 24 h of incubation at 36° C., the MIC reading was taken with the naked eye.

The minimum inhibitory concentration (MIC) assay was performed with reference to the Clinical and Laboratory Standards Institute (CLSI) guidelines.

| Strain (gram-negative bacteria) | Strain ID | AMR gene | ID-CAMHB, MIC, μg/mL | | | |
|---|---|---|---|---|---|---|
| | | | Cefiderocol | Compound 1 | Compound 2 | Compound 3 |
| Carbapenem-resistant *Acinetobacter baumannii* (CRAB, *Acinetobacter baumannii*) | FDA-CDC AR-BANK#0036 | strB, OXA-65, OXA-24, strA, sul2 | 0.5 | 0.25 | 0.5 | 0.25 |
| | FDA-CDC AR-BANK#0052 | OXA-58, OXA-100, sul2 | 0.125 | 0.125 | 0.125 | 0.125 |
| | FDA-CDC AR-BANK#0063 | OXA-23, OXA-65, OXA-24, sul2 | 4 | 32 | 4 | >32 |
| | FDA-CDC AR-BANK#0070 | OXA-58, OXA-100, sul2 | 0.0625 | 0.125 | 0.25 | 0.125 |
| | FDA-CDC AR-BANK#0101 | strB, OXA-65, OXA-24, strA, sul2 | 0.5 | 1 | 1 | 0.5 |
| Carbapenem-resistant Enterobacteriaceae (CRE, *Klebsiella pneumoniae*) | FDA-CDC AR-BANK#0361 | TEM-1; SHV-12; KPC-2 | 1 | 0.5 | 1 | 0.5 |
| | FDA-CDC AR-BANK#0362 | TEM-1; SHV-11; KPC-2 | 0.5 | 0.25 | 0.25 | 0.125 |
| | FDA-CDC AR-BANK#0363 | TEM-1; SHV-12; KPC-2 | 0.25 | 0.125 | 0.5 | 0.125 |
| | FDA-CDC AR-BANK#0438 | aph(3')-Ia, dfrA12, KPC-3, OmpK35, oqxA, oqxB, SHV-11 | 2 | 0.5 | 1 | 0.25 |
| | FDA-CDC AR-BANK#0453 | KPC-3, OmpK35, oqxA, oqxB, SHV-11, TEM-1B | 1 | 1 | 1 | 0.5 |
| Carbapenem-resistant *Pseudomonas aeruginosa* (CRPA, *Pseudomonas aeruginosa*) | FDA-CDC AR-BANK#0439 | aac(6')-Il, aadA1b, BCR1, IMP-18, OXA-50 | 0.5 | 0.125 | 0.5 | 0.125 |
| | FDA-CDC AR-BANK#0441 | KPC-2 | 1 | 2 | 8 | 2 |
| | FDA-CDC AR-BANK#0444 | aac(6')-Il, dfrB5, OXA-4, tet(G), VIM-2 | 1 | 2 | 4 | 2 |
| | FDA-CDC AR-BANK#0457 | aadA6, VIM-2 | 0.25 | 0.125 | 0.25 | 0.25 |
| Control strain* (*Escherichia coli*) | ATCC 25922 | — | 0.0625 | 0.0625 | 0.125 | 0.0625 |
| Control strain* (*Pseudomonas aeruginosa*) | ATCC 27853 | — | 0.0625 | 0.125 | 0.0625 | 0.25 |

Test Example 2: Pharmacokinetic Study of Test Compounds in Cynomolgus Monkeys 1. Sample Preparation An appropriate amount of a test compound was weighed precisely and added to a container, and 0.9% sodium chloride injection and 0.2 M NaOH solution were added thereto in an ice bath until the test compound was completely dissolved, so that a sample solution at a concentration of 2 mg/mL was obtained followed by storage at 2-8° C. for later use.

2. Test Animals

Species and strain: cynomolgus monkey

Animal grade: general grade

Animal source: Guangxi Xiongsen Primate Experimental Animal Breeding Development Co., Ltd.

Number of the using of laboratory animal: SYXK (Su) 2019-0012

3. Test Method 6 cynomolgus monkeys (half male and half female) were selected and randomly divided into 3 groups with 1 animal/sex in each group. The cynomolgus monkeys were administered with the test sample at a dose of 10 mg/kg by the single intravenous infusion. Blood samples were collected from each group of animals at the following time points: before administration, and 5 min, 15 min, 0.5 h, 1 h, 2 h, 4 h, 6 h, and 8 h after administration. In the test, the concentration of each test compound in the plasma of the cynomolgus monkey was detected by the LC-MS/MS method, and the lower limits of quantification of the analysis methods for the plasma samples were all 1 μg/mL. The plasma concentration data were analyzed by the non-compartmental analysis (NCA) of the analysis software for pharmacokinetic data, WinNonlin, pharmacokinetic parameters were calculated, and pharmacokinetic characteristics of the test compounds in cynomolgus monkeys after administration were investigated, with the results shown in the following table.

| Sample | Animal No. | $t_{1/2}$ (h) | Tmax (h) | Cmax (ug/mL) | AUC last (h*ug/mL) | AUCinf (h*ug/mL) | Vd (mL/kg) | CL (mL/h/kg) | MRT (h) |
|---|---|---|---|---|---|---|---|---|---|
| Compound 1 | 2073541 | 0.62 | 0.08 | 35.48 | 29.29 | 32.94 | 270.05 | 303.57 | 0.64 |
| | 2073542 | 0.56 | 0.08 | 30.64 | 23.44 | 25.64 | 313.34 | 390.01 | 0.62 |
| Compound 3 | 2073543 | 2.57 | 0.08 | 55.18 | 148.87 | 166.33 | 222.96 | 60.12 | 2.50 |
| | 2073544 | 2.26 | 0.08 | 48.60 | 140.08 | 153.20 | 213.11 | 65.27 | 2.49 |
| Cefiderocol | 2073545 | 0.86 | 0.08 | 30.53 | 26.21 | 32.39 | 380.98 | 308.70 | 0.70 |
| | 2073546 | 0.75 | 0.08 | 24.33 | 23.94 | 28.35 | 379.63 | 352.76 | 0.70 |

The compounds of the present disclosure are superior in terms of Cmax and AUC as compared to cefiderocol.

Test Example 3: Pharmacokinetic Study of Test Compound in ICR Mice

1. Sample Preparation

The formulation for administration was prepared on ice. A proper amount of the test compound was precisely weighed out, and a 90% volume of normal saline was slowly added. The mixture was ultrasonically stirred in an ice-water bath until no large pieces existed. After the mixture was well mixed, a 1 M NaOH solution was added in small portions using a pipette. After the test sample was completely dissolved as seen by the naked eye, the pH value was measured, and the solution was brought to the final volume to give the formulation for subcutaneous injection with the desired concentration.

2. Test Animals

Species and strain: ICR mice

Animal grade: SPF

Animal source: Medicilon: 999M-018

3. Test Method

The test sample was administered by subcutaneous injection, and the administration regimen is shown in the table below.

| | Animal Number | | Administration | | | | | |
|---|---|---|---|---|---|---|---|---|
| Group | Male | Female | Test compound | Test compound Dose (mg/kg) | Test compound Concentration of solution (mg/mL) | Volume of Administration (mL/kg) | Route of administration* | Collected sample |
| 1 | 12 | 12 | Cefiderocol | 100 | 10 | 10 | Subcutaneous injection | Plasma |
| 2 | 12 | 12 | Compound 3 | 10 | 1 | 10 | Subcutaneous injection | Plasma |
| 3 | 12 | 12 | Compound 3 | 100 | 10 | 10 | Subcutaneous injection | Plasma |

Administration by subcutaneous injection: 3 mice/sex/time point; blood samples were collected at 9 time points: 0.083 h, 0.25 h, 0.5 h, 1 h, 2 h, 4 h, 6 h, 8 h and 24 h after administration. The collected blood samples were placed in EDTA-$K_2$ anticoagulation blood collection tubes. The collected whole blood was placed on ice and centrifuged at 6800 g at 2-8° C. for 6 min to separate plasma within 1 h. After the centrifugation, the plasma was transferred to a centrifuge tube to which a plasma stabilizer had been added in advance (plasma:concentrated phosphoric acid=100:0.2; for example, 1 μL of 10% concentrated phosphoric acid was added to 50 μL of plasma). All the animals were subjected to careful clinical observation before administration and at each of the blood collection time points after administration, and the adverse reaction symptoms in the animals were recorded.

Test results: The pharmacokinetic data for each group are shown below.

| Pharmacokinetic parameter | | Cefiderocol | Compound 3 | Compound 3 |
|---|---|---|---|---|
| Dose | $mg \cdot kg^{-1}$ | 100 | 10 | 100 |
| $K_{el}$ | $h^{-1}$ | 1.45 | 1.04 | 1.64 |
| $T_{1/2}$ | h | 0.477 | 0.665 | 0.421 |
| $t_{max}$ | h | 0.250 | 0.250 | 0.500 |
| $C_{max}$ | $ug \cdot mL^{-1}$ | 362.8 | 113.7 | 935.8 |
| $AUC_{0-t}$ | $h \cdot ug \cdot mL^{-1}$ | 260.9 | 108.7 | 1102.4 |
| $AUC_{0-inf}$ | $h \cdot ug \cdot mL^{-1}$ | 261.1 | 110.0 | 1104.3 |
| $AUMC_{0-t}$ | $h \cdot h \cdot ug \cdot mL^{-1}$ | 150.3 | 80.3 | 871.4 |
| $AUMC_{0-inf}$ | $h \cdot h \cdot ug \cdot mL^{-1}$ | 150.7 | 86.9 | 880.4 |
| $MRT_{PO}$ | h | 0.577 | 0.790 | 0.797 |

The exposure of the compound of the present disclosure in mice was 4.2 times greater than that of cefiderocol.

The invention claimed is:

1. A compound of formula I or a pharmaceutically acceptable salt thereof,

I

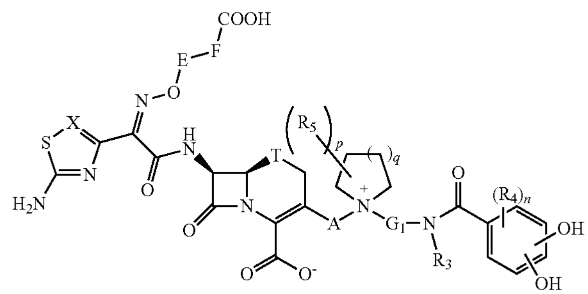

wherein,

X is N, CH or C—Cl;

T is S, S═O, $CH_2$ or O;

E is

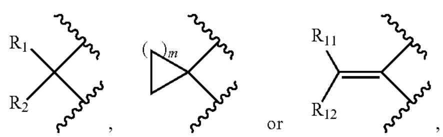

wherein $R_1$ and $R_2$ are each independently selected from the group consisting of hydrogen, halogen, phenyl, alkylthio, and alkyl optionally substituted with carbamoyl; $R_{11}$ and $R_{12}$ are each independently selected from the group consisting of hydrogen, carboxyl, and alkyl optionally substituted with carbamoyl; m is an integer of 1-5;

F is a single bond;

A is $C_1$-$C_6$ alkylene, $C_2$-$C_6$ alkenylene or $C_2$-$C_6$ alkynylene;

each $R_5$ is independently selected from the group consisting of halogen, hydroxy, $C_1$-$C_6$ alkyl, $C_1$-$C_6$ alkoxy, $C_1$-$C_6$ haloalkyl and $C_1$-$C_6$ haloalkoxy;

$G_1$ is

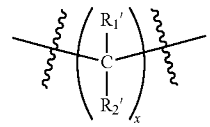

$R_1$' and $R_2$' are each independently selected from the group consisting of hydrogen, halogen, hydroxy, $C_1$-$C_6$ alkyl, $C_1$-$C_6$ alkoxy, $C_1$-$C_6$ haloalkyl and $C_1$-$C_6$ haloalkoxy;

$R_3$ is $C_1$-$C_6$ alkyl substituted with

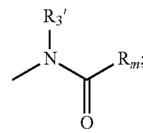

$R_3$' is selected from the group consisting of hydrogen, hydroxy, $C_1$-$C_6$ alkyl and $C_1$-$C_6$ alkoxy, wherein the alkyl and alkoxy are optionally substituted with one or more substituents selected from the group consisting of $C_1$-$C_6$ alkyl, halogen, hydroxy, sulfhydryl, —$NR_iR_j$,

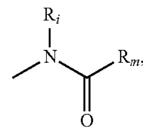

oxo, thio, —C(O)$R_k$, —C(O)O$R_k$, —C(S)$R_k$, nitro, cyano, $C_1$-$C_6$ alkoxy and $C_1$-$C_6$ alkylthioether group;

each $R_m$ is independently selected from the group consisting of hydrogen, $C_1$-$C_6$ alkyl, $C_1$-$C_6$ alkoxy, hydroxy, 6- to 10-membered aryl and 5- to 8-membered heteroaryl, wherein the alkyl, alkoxy, aryl and heteroaryl are optionally substituted with one or more substituents selected from the group consisting of $C_1$-$C_6$ alkyl, halogen, hydroxy, sulfhydryl, amino, carboxyl, nitro, cyano and $C_1$-$C_6$ alkoxy;

each $R_4$ is independently selected from the group consisting of halogen, hydroxy, sulfhydryl and —$NR_iR_j$;

$R_i$ and $R_j$ are each independently selected from the group consisting of hydrogen, hydroxy, $C_1$-$C_6$ alkyl and $C_1$-$C_6$ alkoxy;

each $R_k$ is independently selected from the group consisting of hydrogen, $C_1$-$C_6$ alkyl, $C_1$-$C_6$ haloalkyl, hydroxy, $C_1$-$C_6$ alkoxy and —$NR_iR_j$, wherein the alkyl, haloalkyl and alkoxy are optionally substituted with one or more substituents selected from the group consisting of $C_1$-$C_6$ alkyl, halogen, hydroxy, sulfhydryl, —$NR_iR_j$, oxo, thio, carboxyl, nitro, cyano, $C_1$-$C_6$ alkoxy, $C_1$-$C_6$ alkylthioether group, 3- to 6-membered cycloalkyl, 3- to 6-membered heterocyclyl, 6- to 10-membered aryl and 5- to 8-membered heteroaryl;

p is an integer of 0-5;

q is an integer of 0-5;

x is 3;

n is an integer of 0-3.

2. The compound or the pharmaceutically acceptable salt thereof according to claim 1, wherein A is $C_1$-$C_6$ alkylene.

3. The compound or the pharmaceutically acceptable salt thereof according to claim 1, wherein $R_1$' and $R_2$' are both hydrogen atoms.

4. The compound or the pharmaceutically acceptable salt thereof according to claim 1, wherein $R_3$ is selected from $C_3$-$C_6$ alkyl substituted with

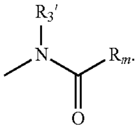

5. The compound or the pharmaceutically acceptable salt thereof according to claim 1, wherein

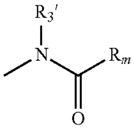

is

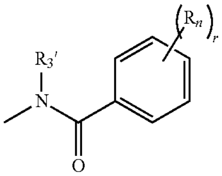

, wherein each $R_n$ is independently selected from the group consisting of $C_1$-$C_6$ alkyl, hydroxy and halogen, and r is independently an integer of 0-5.

6. The compound or the pharmaceutically acceptable salt thereof according to claim 1, wherein $R_3$' is selected from the group consisting of hydrogen and $C_1$-$C_6$alkyl substituted with

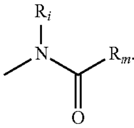

7. The compound or the pharmaceutically acceptable salt thereof according to claim 1, wherein

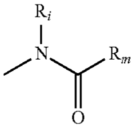

is

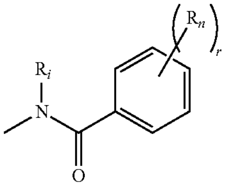

, wherein each $R_n$ is independently selected from the group consisting of $C_1$-$C_6$ alkyl, hydroxy and halogen, and r is independently an integer of 0-5.

8. The compound or the pharmaceutically acceptable salt thereof according to claim 1, wherein the compound of formula I is selected from

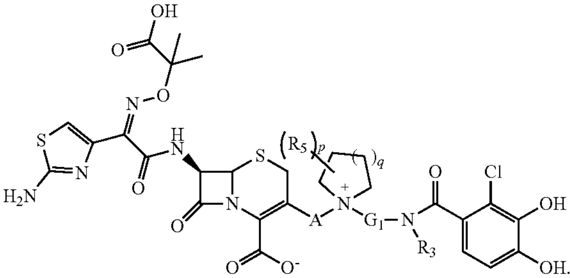

9. The compound or the pharmaceutically acceptable salt thereof according to claim 1, being selected from

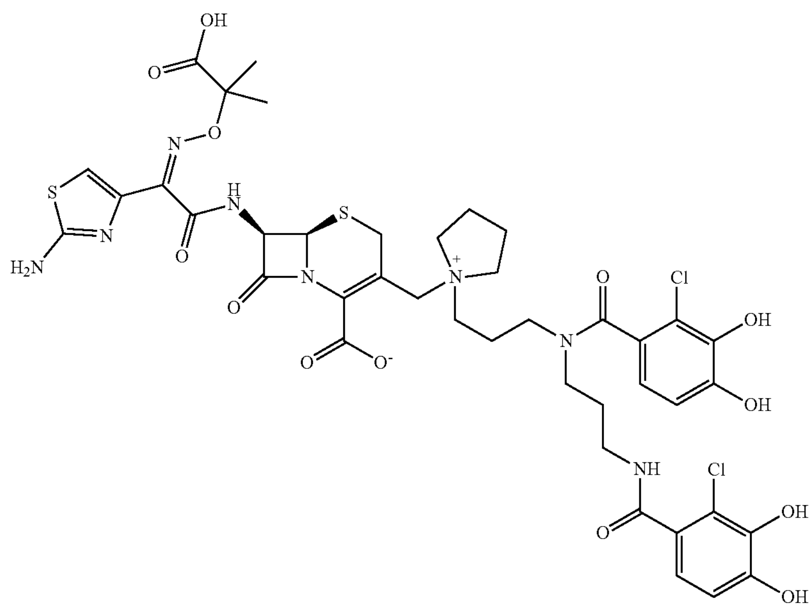

or a pharmaceutically acceptable salt thereof.

10. An isotopically substituted form of the compound or the pharmaceutically acceptable salt thereof according to claim 1.

11. A pharmaceutical composition comprising the compound or the pharmaceutically acceptable salt thereof according to claim 1 and a pharmaceutically acceptable carrier, diluent or excipient.

12. A method of treating or preventing a disease caused by gram-negative bacteria in a subject in need thereof, the method comprising administering to the subject the compound or the pharmaceutically acceptable salt thereof according to claim 1.

13. A method of treating or preventing a disease caused by pathogenic bacteria in a subject in need thereof, the method comprising administering to the subject the compound or the pharmaceutically acceptable salt thereof according to claim 1.

14. The compound or the pharmaceutically acceptable salt thereof according to claim 1, wherein

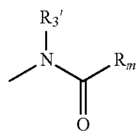

is

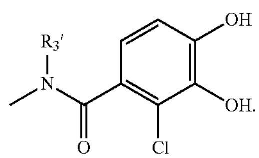

15. The compound or the pharmaceutically acceptable salt thereof according to claim 1, wherein

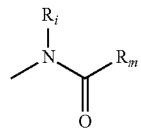

is

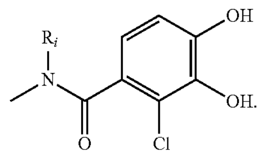

16. The isotopically substituted form of the compound or the pharmaceutically acceptable salt thereof according to claim 10, wherein the isotopic substitution is a substitution with a deuterium atom.

17. The method according to claim 12, wherein the disease is selected from the group consisting of airway infectious diseases, urinary system infectious diseases, respiratory system infectious diseases, septicemia, nephritis, cholecystitis, oral infectious diseases, endocarditis, pneumonia, bone marrow membrane myelitis, otitis media, enteritis, empyema, traumatic infectious diseases and opportunistic infections.

18. The method according to claim 12, wherein the gram-negative bacteria is selected from the group consisting of *E. coli, Klebsiella, Serratia, Enterobacter, Citrobacter, Morganella, Providencia, Proteus, Haemophilus, Moraxella, Pseudomonas aeruginosa, Pseudomonas* other than *P. aeruginosa, Stenotrophomonas, Burkholderia* and *Acinetobacter*.

* * * * *